(12) United States Patent
Johnson et al.

(10) Patent No.: US 9,422,547 B1
(45) Date of Patent: Aug. 23, 2016

(54) RECOMBINANT FUSION PROTEINS AND LIBRARIES FROM IMMUNE CELL REPERTOIRES

(71) Applicant: Gigagen, Inc., San Francisco, CA (US)

(72) Inventors: David Scott Johnson, San Francisco, CA (US); Adam Adler, Belmont, CA (US); Rena Mizrahi, Pacifica, CA (US)

(73) Assignee: GigaGen, Inc., South San Francisco, CA (US)

( * ) Notice: Subject to any disclaimer, the term of this patent is extended or adjusted under 35 U.S.C. 154(b) by 0 days.

(21) Appl. No.: 14/734,953

(22) Filed: Jun. 9, 2015

(51) Int. Cl.
*C40B 50/06* (2006.01)
*C12N 15/10* (2006.01)

(52) U.S. Cl.
CPC ............ *C12N 15/1037* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 5,830,663 A | 11/1998 | Embleton et al. | |
| 6,013,445 A | 1/2000 | Albrecht et al. | |
| 6,858,412 B2 | 2/2005 | Willis et al. | |
| 7,749,697 B2 | 7/2010 | Oleksiewicz et al. | |
| 2005/0041525 A1 | 2/2005 | Pugia et al. | |
| 2006/0108012 A1 | 5/2006 | Barrow et al. | |
| 2006/0134599 A1 | 6/2006 | Toner et al. | |
| 2007/0141048 A1 | 6/2007 | Oleksiewicz et al. | |
| 2009/0098555 A1 | 4/2009 | Roth et al. | |
| 2010/0021896 A1 | 1/2010 | Han | |
| 2010/0330571 A1 | 12/2010 | Robbins et al. | |
| 2011/0059556 A1 | 3/2011 | Strey et al. | |
| 2011/0201009 A1 | 8/2011 | Quake et al. | |
| 2013/0296535 A1 | 11/2013 | Church et al. | |
| 2014/0057799 A1 | 2/2014 | Johnson et al. | |
| 2015/0125865 A1 | 5/2015 | Johnson et al. | |
| 2015/0154352 A1 | 6/2015 | Johnson et al. | |

FOREIGN PATENT DOCUMENTS

| | | |
|---|---|---|
| EP | 1516929 A2 | 3/2005 |
| JP | 2002-522067 A | 7/2002 |
| JP | 2009-518053 A | 5/2009 |
| KR | 10-2007-0031923 A | 3/2007 |
| KR | 10-2012-0004939 A | 1/2012 |
| WO | WO 93/03151 A1 | 2/1993 |
| WO | WO 2009/049889 A1 | 4/2009 |
| WO | WO 2011/139371 A1 | 11/2011 |
| WO | WO 2012/083225 A1 | 6/2012 |
| WO | WO 2012/104851 A1 | 8/2012 |
| WO | WO 2013/096643 A1 | 6/2013 |
| WO | WO 2013/192570 A1 | 12/2013 |
| WO | WO 2014/011735 A1 | 1/2014 |

OTHER PUBLICATIONS

Communication pursuant to Article 94(3) EPC for European Patent Application No. EP 11848932.7, Mar. 13, 2015, 4 Pages.
Supplementary European Search Report for European Patent Application No. EP 11848932.7, Apr. 11, 2014, 10 Pages.
Office Action for U.S. Appl. No. 13/993,047, Jun. 30, 2015, 28 Pages.

(Continued)

*Primary Examiner* — Christian Boesen
(74) *Attorney, Agent, or Firm* — Fenwick & West LLP

(57) ABSTRACT

Disclosed herein are methods and compositions for generating a repertoire of recombinant fusion polypeptides from immune cells, and uses thereof.

16 Claims, 9 Drawing Sheets

(56) References Cited

OTHER PUBLICATIONS

PCT International Search Report and Written Opinion, Application No. PCT/US2011/065600, Apr. 9, 2012, 16 pages.

PCT International Search Report and Written Opinion, Application No. PCT/US2012/070989, Dec. 14, 2013, 9 pages.

PCT International Search Report and Written Opinion, Application No. PCT/US2013/047142, Oct. 18, 2013, 11 Pages.

PCT International Search Report and Written Opinion, Application No. PCT/US2013/049872, Oct. 8, 2013, 17 Pages.

Bonarius, H., et al., "Monitoring the T-Cell Receptor Repertoire at Single-Clone Resolution," PLOS One, Public Library of Science, US, vol. 1 1, No. 1, Dec. 20, 2006, pp. E55 1-10.

Boyd, S., et al., "Measurement and Clinical Monitoring of Human Lymphocyte Clonality by Massively Parallel V-D-J Pyrosequencing," Science Translational Medicine, Dec. 23, 2009, vol. 1, Issue 12 12ra23, pp. 1-8.

Brouzes, E., et al., "Droplet microfluidic technology for single-cell high-throughput screening," PNAS, Aug. 25, 2009, vol. 106, No. 34, pp. 14195-14200.

Chial, H., "Tumor Suppressor (TS) genes and the two-hit hypothesis," Nature Education 1 (1):177, 6 Pages, [online] 2008 [retrieved on Jun. 26, 2015] retrieved from the Internet <URL:http://www.nature.com/scitable/nated/topicpage/Tumor-Suppressor-TS-Genes-and-the-Two-887>.

Embleton, M.J., et al., "In-cell PCR from mRNA: amplifying and linking the rearranged immunoglobulin heavy and light chain V-genes within single cells," Nucleic Acids Research, 1992, vol. 20, No. 15, pp. 3831-3837.

Freeman et al., "Profiling the T-cell receptor beta-chain repertoire by massively parallel sequencing" Genome Research, 2009, vol. 19, No. 10, pp. 1817-1824.

Hardenbol, P., et al., "Multiplexed genotyping with sequence-tagged molecular inversion probes," Nature Biotechnology, Jun. 2003, vol. 21, No. 6, pp. 673-678.

Hardenbol, P., et al., "Highly Multiplexed molecular inversion probe genotyping: Over 10,000 targeted SNPs genotyped in a single tube assay," Genome Research, 2005, vol. 15, pp. 269-275.

Hviid, T.V., In-Cell PCR Method for Specific Genotyping of Genomic DNA from One Individual in a Mixture of Cells from Two Individuals: A Model Study with Specific Relevance to Prenatal Diagnosis Based on Fetal Cells in Maternal Blood, Clinical Chemistry, 2002, vol. 48, pp. 2115-2123.

Johnston, K.P., et al., "Water-in-Carbon Dioxide Microemulsions: An Environment for Hydrophiles Including Proteins," Science, Feb. 2, 1996, vol. 271, pp. 624-626.

Johnston, D., et al., "De novo discovery of a tissue-specific gene regulatory module in a chordate," Genome Research, 2005, vol. 15, pp. 1315-1324.

Kiss, M.M., et al., "High-Throughput Quantitative Polymerase Chain Reaction in Picoliter Droplets," Anal. Chem., 2005, vol. 80, pp. 8975-8981.

Maheswaran, S., et al., "Detection of Mutations in EGFR in Circulating Lung-Cancer Cells," The New England Journal of Medicine, 2008, vol. 359, pp. 366-377.

Monod, M.Y., et al., "IMGT/JunctionAnalysis: the first tool for the analysis of the immunoglobulin and T cell receptor complex V-J and V-D-J Junctions," Bioinformatics, 2004, vol. 20, pp. i379-i385.

Nagrath, S., et al., "Isolation of rare circulating tumour cells in cancer patients by microchip technology," Nature, 2007, vol. 450, pp. 1235-1239.

Porreca, G., et al., "Multiplex amplification of large sets of human exons," Nature Methods, Nov. 2007, vol. 4, No. 11, pp. 931-936.

Robins, H., et al., "Comprehensive assessment of T-cell receptor β-chain diversity in αβ T cells," Blood, 2009, vol. 114, pp. 4099-4107.

Robins, H., et al., "Overlap and Effective Size of the Human CD8[+] T Cell Receptor Repertoire," Science Translational Medicine, Sep. 1, 2010, vol. 2, Issue 47 47ra64, pp. 1-9.

Sandberg, Y., et al., "Biomed-2 Multiplex Immunoglobulin/T-Cell Receptor Polymerase Chain Reaction Protocols Can Reliably Replace Southern Blot Analysis in routine Clonality Diagnostics," Journal of Molecular Diagnostics, Oct. 2005, vol. 7, No. 4, pp. 495-503.

Shigematsu, H., et al., "Clinical and Biological Features Associated With Epidermal Growth Factor Receptor Gene Mutations in Lung Cancers," Journal of the National Cancer Institute, 2005, vol. 97, pp. 339-346.

Van Dongen, J.J.M., et al., Design and standardization of PCR primers and protocols for detection of clonal immunoglobulin and T-cell receptor gene recombinations in Leukemia, 2003, vol. 17, pp. 2257-2317.

Zeng, Y., et al., High-Performance Single Cell Genetic Analysis Using Microfluidic Emulsion Generator Arrays, Anal. Chem., 2010, vol. 82, pp. 3183-3190.

Pre-Interview First Office Action for U.S. Appl. No. 14/539,915, Mar. 2, 2016, 21 pages.

Office Action for U.S. Appl. No. 13/993,047, Mar. 22, 2016, 31 pages.

a Left primer for target #1
b Right primer for target #1
c Primer region complementary to d
d Primer region complementary to c
e Left primer for target #2
f Right primer for target #2
g Polynucleic acid target #1
h Polynucleic acid target #2
i Cell membrane
j Physical reaction container or emulsion droplet a Left primer for target #1
b Right primer for target #1
c Primer region complementary to d
d Primer region complementary to c
e Left primer for target #2
f Right primer for target #2
g Polynucleic acid target #1
h Polynucleic acid target #2
j Physical reaction container or emulsion droplet c Product region complementary to d
d Product region complementary to c
g Polynucleic acid target #1
h Polynucleic acid target #2
j Physical reaction container or emulsion droplet

RECOMBINANT FUSION PROTEINS AND LIBRARIES FROM IMMUNE CELL REPERTOIRES

SEQUENCE LISTING

The instant application contains a Sequence Listing which has been submitted electronically in ASCII format and is hereby incorporated by reference in its entirety. Said ASCII copy, created on Aug. 7, 2015, is named 29023US_CRF_sequencelisting.txt and is 34,094 bytes in size.

FIELD OF THE INVENTION

The invention relates to methods and compositions for protein engineering for use in biomedical applications.

BACKGROUND OF THE INVENTION

Antibody therapeutics are increasingly used by pharmaceutical companies to treat intractable diseases such as cancer (Carter 2006 Nature Reviews Immunology 6:343-357). However, the process of antibody drug discovery is expensive and tedious, and has proceeded by identification of an antigen, and then the isolation and production of antibodies with activity against the antigen. Furthermore, affinity selection and expression of a limited number of antibodies from this selection has provided a mechanism of treatment that is narrower than that provided by the body. However, artificial generation of a representative immune repertoire from an individual with cognate paired heavy and light chain immunoglobulin or T cell receptors has not been achieved.

Individuals that have been exposed to disease naturally produce antibodies against antigens associated with that disease. Therefore, what is needed are improved methods of high throughput generation of recombinant fusion proteins comprising both heavy and light chain variable domains so it is possible to use natural immune repertoires in treatment and pharmaceutical discovery and development.

SUMMARY OF THE INVENTION

Disclosed herein are methods and compositions of generating a recombinant fusion polypeptide. In an embodiment, disclosed herein is a method for preparing a recombinant immunoglobulin library, comprising: providing primary immune cells from at least one mammalian donor; isolating in a plurality of monodisperse droplets single immune cells from said primary immune cells; generating a plurality of recombinant fusion polynucleotides each comprising a first polynucleotide encoding a heavy chain variable domain and a second polynucleotide encoding a light chain variable domain, wherein said heavy chain variable domain and light chain variable domain on each of said plurality of recombinant fusion polynucleotides are a cognate pair from one of said isolated primary immune cells, wherein each of said plurality of recombinant fusion polynucleotides further comprise a linker polynucleotide linking said first and second polynucleotides; circularizing each of said plurality of linear recombinant fusion polynucleotides; and inserting a third polynucleotide comprising a sequence encoding a promoter and a sequence encoding a constant region between said first and second polynucleotide in each of said circularized recombinant fusion polynucleotides, thereby generating at least 1,000 unique recombinant immunoglobulin expression constructs, thereby generating a recombinant immunoglobulin library.

In an embodiment, the method further comprises inserting said at least 1,000 recombinant immunoglobulin expression constructs into a plurality of host cells; and expressing said at least 1,000 recombinant immunoglobulin expression constructs in said plurality of host cells, thereby generating a recombinant immunoglobulin library comprising at least 1,000 unique recombinant immunoglobulins, wherein each of said at least 1,000 unique recombinant immunoglobulins comprises a linked heavy chain and light chain variable domain cognate pair from a single isolated cell, thereby generating a recombinant immunoglobulin library.

In an embodiment, the recombinant immunoglobulin library encodes least 10,000, 100,000, or 1,000,000 unique recombinant immunoglobulin proteins. In an embodiment, the at least one mammalian donor is selected based on a medical criterion. In an embodiment, the medical criterion comprises a heightened immune response to hepatitis B, rabies, tetanus toxin, varicella-zoster, cytomegalovirus, or pneumococcus.

In an embodiment, the at least one mammalian donor was exposed to an antigen of interest or a pathogen. In an embodiment, the antigen of interest is a tumor antigen selected from the group consisting of: CD19, CD20, CD22, CD52, epidermal growth factor receptor (EGFR), human epidermal growth factor receptor 2 (HER2), tumor necrosis factor receptor superfamily, member 10a (TRAILR1), receptor activator of nuclear factor kappa-B ligand (RANKL), insulin-like growth factor 1 receptor (IGF1R), epithelial cell adhesion molecule (EpCAM), carcinoembryonic antigen (CEA), and mucin 5AC. In an embodiment, the antigen of interest is an autoimmune antigen selected from the group consisting of: thrombin, nicotinic acetylcholine receptor, thyroglobulin, TSH receptor, glutamate decarboxylase, phospholipase-A2-receptor (PLA2R), and muscle specific kinase (MUSK).

In an embodiment, the at least one mammalian donor was immunized against a pathogen. In an embodiment, the at least one mammalian donor has an autoimmune disease or cancer. In an embodiment, the at least one mammalian donor has idiopathic (immune) thrombocytopenic purpura (ITP), Kawasaki's vasculitis, B cell chronic lymphocytic leukemia (CLL), or primary immunodeficiencies. In an embodiment, the recombinant immunoglobulin expression construct is an expression vector.

Also provided herein is a method for preparing a plurality of recombinant immunoglobulin expression constructs, comprising: providing a plurality of recombinant fusion polynucleotides each comprising a first polynucleotide encoding a first variable domain, a second polynucleotide encoding a second variable domain, and a linker polynucleotide linking the first and second polynucleotides; expressing a plurality of recombinant fusion polypeptides encoded by said plurality of recombinant fusion polynucleotides to display said plurality of recombinant fusion polypeptides on a plurality of surfaces; enriching said plurality of recombinant fusion polynucleotides for binding to an antigen by exposing said plurality of surfaces to said antigen and selecting based on binding between said antigen and each of said plurality of recombinant fusion polypeptides; circularizing one or more of said enriched recombinant fusion polynucleotides; and inserting a third polynucleotide comprising a sequence encoding a promoter and a sequence encoding a constant region between said first and second polynucleotide in each of said circularized enriched recombinant fusion polynucleotides, thereby generating a plurality of recombinant immunoglobulin expression constructs.

In an embodiment, the method further comprises inserting said plurality of recombinant immunoglobulin expression constructs into a plurality of host cells; and expressing said plurality of recombinant immunoglobulin expression construct in said plurality of host cells, thereby generating a recombinant immunoglobulin library, wherein each recombinant immunoglobulin comprises a linked heavy chain and light chain variable domain cognate pair from a single isolated cell.

In an embodiment, the first variable domain is from an immunoglobulin heavy chain, and said second variable domain is from an immunoglobulin light chain. In an embodiment, the plurality of recombinant immunoglobulin expression constructs comprises at least 1,000, 10,000, or 100,000 unique cognate pairs of heavy chain and light chain encoding sequences.

Also provided herein is a method of generating an immunoglobulin library, comprising: providing a plurality of circularized polynucleotide constructs, each comprising a first polynucleotide, a second polynucleotide, and a linker polynucleotide linking the first and second polynucleotides, wherein said first polynucleotide comprises a region encoding a first variable domain from a single isolated cell, wherein said second polynucleotide comprises a region encoding a second variable domain from said single isolated cell, and wherein each of said plurality of circularized polynucleotide constructs comprises a cognate pair of linked first and second variable domains from a single isolated cell; inserting a third polynucleotide comprising a sequence encoding a promoter and a sequence encoding a constant region between said first and second polynucleotide in each of said circularized recombinant fusion polynucleotides, thereby generating a plurality of recombinant immunoglobulin expression construct; inserting said plurality of recombinant immunoglobulin expression constructs into a plurality of host cells; and expressing said plurality of recombinant immunoglobulin expression construct in said plurality of host cells, thereby generating a recombinant immunoglobulin library comprising a plurality of recombinant immunoglobulins, wherein each of said plurality of recombinant immunoglobulins comprises a linked heavy chain variable domain and light chain variable domain cognate pair from a single isolated cell.

In an embodiment, the insertion of said third polynucleotide is performed in parallel for said plurality of circularized polynucleotide constructs. In an embodiment, at least one recombinant immunoglobulin from said recombinant immunoglobulin library specifically binds to a *Streptococcus pneumonia* epitope, a *Hemophilis influenza* epitope, or a *Klebsiella pneumonia* epitope. In an embodiment, the first variable domain is from an immunoglobulin heavy chain, and said second variable domain is from an immunoglobulin light chain. In an embodiment, the plurality of recombinant fusion protein expression constructs are expression vectors. In an embodiment, the insertion of said third polynucleotide comprises a method selected from the group consisting of: Gibson assembly, site-specific digestion and ligation, and targeted recombination.

Also provided herein is a composition comprising a pool of at least 10,000 monodisperse aqueous droplets in an oil solution, wherein said aqueous droplets each have a diameter of between 1 micron and 200 microns, wherein each of said aqueous droplets have an outer boundary comprising a surfactant, and wherein a plurality of said at least 10,000 monodisperse aqueous droplets comprise a first probe comprising a first polynucleotide having a length of between 15 and 120 nucleotides, wherein said first probe is complementary to a first subsequence of a polynucleotide encoding a constant domain or poly(A) tail of an antibody or T cell receptor, and a second probe comprising a second polynucleotide having a length of between 15 and 120 nucleotides, wherein said second polynucleotide is complementary to a second subsequence of a polynucleotide encoding a constant domain or poly(A) tail of an antibody or T cell receptor; wherein said first and second probes are attached to at least one particle.

In an embodiment, the first and second nucleic acid probes are bound to a particle. In an embodiment, the particle is a bead comprising agarose, glass, chemical polymers, or magnetic materials. In an embodiment, the probes comprise biotin and wherein said particle comprises streptavidin bound to the surface of the particle. In an embodiment, the composition comprises a covalent bond between said first probe or said second probe and said particle. In an embodiment, each of said plurality of monodisperse aqueous droplets further comprise reagents for overlap extension RT-PCR. In an embodiment, the first probe is bound to a polynucleotide encoding a light chain variable domain from a single isolated cell, and wherein said second probe is bound to a polynucleotide encoding a heavy chain variable domain from said single isolated cell.

Also provided herein is a method for preparing a recombinant fusion protein expression construct, comprising: providing a linear polynucleotide construct comprising a first polynucleotide encoding a first variable domain, a second polynucleotide encoding a second variable domain, and a linker polynucleotide linking the first and second polynucleotides; circularizing said linear polynucleotide, so that said first and second variable domain are connected by said linker polynucleotide and a second polynucleotide; and inserting a third polynucleotide encoding a transcriptional modulator, a translational modifier, a constant domain, or an immune effector into the spacer polynucleotide, thereby generating a recombinant fusion protein expression construct.

In an embodiment, the first and second variable domains are from a single cell. In an embodiment, the first variable domain is from an immunoglobulin heavy chain, and said second variable domain is from an immunoglobulin light chain. In an embodiment, the recombinant fusion protein expression construct is an expression vector.

Also provided herein is a method of generating a plurality of circularized polynucleotides, comprising: providing primary immune cells from at least one mammalian donor; isolating single immune cells from said primary immune cells in a plurality of reaction vessels; generating a plurality of linear recombinant fusion polynucleotides each comprising a first polynucleotide encoding a heavy chain variable domain and a second polynucleotide encoding a light chain variable domain from each isolated single immune cell, wherein each of said plurality of linear recombinant fusion polynucleotides further comprise a linker polynucleotide linking said first and second polynucleotides; and circularizing said linear recombinant fusion polynucleotide.

Disclosed herein are methods and compositions of generating a recombinant fusion polypeptide. In an embodiment, the method comprises providing, in a reaction vessel, a lysis solution and a first nucleic acid probe and a second nucleic acid probe, wherein said first and second nucleic acid probes are attached to the same or different substrates, wherein said first nucleic acid probe is capable of hybridizing to a complementary region on first polynucleotide comprising a first variable domain, and wherein said second nucleic acid probe is capable of hybridizing to a complementary region on a second target polynucleotide comprising a second variable domain; wherein said first target polynucleotide comprises a first variable domain, and said second target polynucleotide comprises a second variable domain adding one or more immune cells to said reaction vessel, thereby lysing said one or more immune cells; hybridizing said first probe to said first target polynucleotide; hybridizing said second probe to said second target polynucleotide; and generating a recombinant fusion polynucleotide comprising said first variable domain and said second variable domain.

In an embodiment, the method further comprises isolating said same or different substrates from said lysis solution after hybridization in said reaction vessel. In an embodiment, the method further comprises expressing said recombinant fusion polynucleotide in a host cell, thereby generating a recombinant fusion polypeptide. In an embodiment, the method further comprises purifying the recombinant fusion polypeptide. In an embodiment, said recombinant fusion polypeptide comprises a single chain variable fragment (scFv) or an antibody fragment.

In an embodiment, the method further comprises said recombinant fusion polypeptide is secreted by the host cell. In an embodiment, said recombinant fusion polypeptide comprises at least two unique variable domains from the same antibody from said one or more immune cells. In an embodiment, said recombinant fusion polypeptide comprises at least two unique variable domains form the same T cell receptor from said one or more immune cells. In an embodiment, said host cell is a yeast, insect, bacteria, or mammalian cell.

In an embodiment, the step of generating a recombinant fusion polynucleotide comprises using overlap extension PCR to fuse and amplify the first variable domain and the second variable domain. In an embodiment, the one or more immune cells is a subpopulation of antibody or T-cell receptor producing cells. In an embodiment, the one or more immune cells expresses an antibody or T-cell receptor. In an embodiment, the reaction vessel is a droplet. In an embodiment, the droplet is an aqueous droplet in an oil solution, said aqueous droplet comprising an outer layer comprising a surfactant boundary. In an embodiment, the particle is a bead. In an embodiment, the first nucleic acid probe and said second nucleic acid probe are each between 20 and 130 nucleotides in length. In an embodiment, the first and second nucleic acid probes each are complementary to a subsequence of the constant domain of an antibody or T cell receptor.

In an embodiment, the first nucleic acid probe attached to a particle, said second nucleic acid probe attached to a particle and said one or more immune cells are encapsulated in a reaction vessel. In an embodiment, the one or more immune cells comprise an immune cell population. In an embodiment, the first and second target polynucleotides each encode a portion of a different protein subunit.

In an embodiment, the recombinant fusion polynucleotide is generated by amplification of said first target polynucleotide and said second target polynucleotide and fusing said first and second amplified products. In an embodiment, the amplification is performed using droplet PCR. In an embodiment, the first variable domain and said second variable domain are separated by less than 1,000, 900, 800, 700, 600, 500, 400, 300, 200, 100, 80, 60, 40, or 20 nucleotides in the recombinant fusion polynucleotide.

In an embodiment, the one or more immune cells comprise B cells or plasma cells. In an embodiment, the first variable domain encodes a light chain variable domain polypeptide, and said second variable domain encodes a heavy chain variable domain polypeptide. In an embodiment of the method, a linker polynucleotide is disposed between the first variable domain and the second variable domain in said recombinant fusion polynucleotide.

In an embodiment, the first probe comprises a polynucleotide sequence complementary to a portion of a light chain constant domain encoding polynucleotide, and wherein said second probe comprises a polynucleotide sequence complementary to a portion of a heavy chain constant domain encoding polynucleotide. In an embodiment, the first probe and said second probe comprise oligo(dT) polynucleotides capable of hybridizing to the poly(A) tail of mRNA.

Also provided herein is a method for preparing a recombinant fusion polynucleotide protein expression construct, comprising: providing a polynucleotide construct comprising a first polynucleotide encoding a first variable domain, a second polynucleotide encoding a second variable domain, and a spacer polynucleotide linking the first and second polynucleotides; and inserting a third polynucleotide encoding a transcriptional modulator, a translational modifier, a constant domain, or an immune effector into the spacer polynucleotide, thereby generating said recombinant fusion polynucleotide protein expression construct.

In an embodiment, the variable domains are amplified from a single cell or subpopulation of cells. In an embodiment, the first variable domain is an immunoglobulin heavy chain, and said second variable domain is an immunoglobulin light chain. In an embodiment, the first variable domain is a T cell receptor alpha and said second variable domain is a T cell receptor beta. In an embodiment, the recombinant fusion polynucleotide expression recombinant fusion protein expression construct is an expression vector. In an embodiment, the expression vector is a plasmid or a phagemid. In an embodiment, the insertion of said third polynucleotide into said spacer polynucleotide comprises a method selected from the group consisting of: Gibson assembly, site-specific digestion and ligation, and targeted recombination.

Also provided herein is a recombinant fusion polynucleotide expression recombinant fusion protein expression construct comprising a first polynucleotide encoding a first variable domain, a second polynucleotide encoding a second variable domain, and a spacer polynucleotide linking the first and second polynucleotides, wherein said spacer polynucleotide comprises a transcriptional modulator, a translational modifier, a constant domain, or an immune effector. In an embodiment, the first variable domain and said second variable domain are from a single cell or subpopulation of cells. In an embodiment, the first variable domain is an immunoglobulin heavy chain, and said second variable domain is an immunoglobulin light chain. In an embodiment, the first variable domain is a T cell receptor alpha and said second variable domain is a T cell receptor beta. In an embodiment, the recombinant fusion polynucleotide expression recombinant fusion protein expression construct is an expression vector. In an embodiment, the expression vector is a plasmid or a phagemid.

Also provided herein is a method of generating a recombinant fusion polypeptide, comprising: inserting a recombinant fusion polynucleotide expression recombinant fusion protein expression construct into a host cell, wherein said recombinant fusion polynucleotide expression recombinant fusion protein expression construct comprises a polynucleotide encoding a first variable domain, a second polynucleotide encoding a second variable domain, and a spacer polynucleotide linking the first and second polynucleotides, wherein said spacer polynucleotide comprises a transcriptional modulator, a translational modifier, a constant domain, or an immune effector; expressing the protein expression construct in said host cell, thereby generating a recombinant fusion polypeptide; and purifying said recombinant fusion polypeptide.

In an embodiment, the spacer polynucleotide comprises a transcriptional modulator, a translational modifier, a constant domain, or an immune effector. In an embodiment, the host cell is a yeast, bacteria, or mammalian cell. In an embodiment, the method is used to generate at least 1,000 unique recombinant fusion polypeptides. In an embodiment, the method is used to generate at least 10,000 unique recombinant fusion polypeptides. In an embodiment, the method is used to generate at least 100,000 unique recombinant fusion polypeptides.

Also provided herein is a method of enriching a mixture of unique fusion polypeptides, comprising: providing a polynucleotide construct comprising a first polynucleotide encoding a first variable domain, a second polynucleotide encoding a second variable domain, and a spacer polynucleotide linking the first and second polynucleotides; expressing the polynucleotide construct in a population of host cells to generate a polypeptide comprising said first and second variable domain on the surface of said host cell; enriching for a subpopulation of host cells expressing polypeptides that bind to said antigen of interest; and inserting a third polynucleotide into said spacer polynucleotide in one or more said polynucleotide constructs isolated from said enriched subpopulation, wherein said third polynucleotide comprises a transcriptional modulator, a translational modifier, a constant domain, or an immune effector.

Also provided herein is a composition comprising a pool of at least 10,000 aqueous droplets in an oil solution, wherein said aqueous droplets have a diameter of between 1 micron and 200 microns, and wherein said aqueous droplets have an outer layer comprising a surfactant boundary, and wherein a plurality of said droplets comprise a first probe comprising a first polynucleotide having a length of between 20 and 120 nucleotides, wherein said first polynucleotide is complementary to a first subsequence of a polynucleotide encoding a constant domain of an antibody or T cell receptor, and a second probe comprising a second polynucleotide having a length of between 20 and 120 nucleotides, wherein said second polynucleotide is complementary to a second subsequence of a polynucleotide encoding a constant domain of an antibody or T cell receptor; wherein said first and second probes are attached to at least one particle.

In an embodiment, the pool of at least 10,000 aqueous droplets is monodisperse. In an embodiment, the surfactant boundary separates the aqueous phase in said droplet from the oil solution. In an embodiment, the particle is a spherical bead comprising agarose, glass, chemical polymers, or magnetic materials. In an embodiment, the probes comprise biotin and wherein said particle comprises streptavidin attached to the surface of the particle. In an embodiment, the attachment of said first probe or said second probe to said particle comprises a covalent bond.

In an embodiment, the surfactant boundary comprises a surfactant selected from the group consisting of: a nonionic surfactant, a zwitterionic surfactant, a sulfate, a sulfonate, and a phosphate ester. In an embodiment, the nonionic surfactant is selected from the group consisting of: polyethylene glycol alkyl ether, sorbitan alkyl ester, and polyethylene glycol octophenol ether. In an embodiment, the surfactant boundary comprises sodium lauryl sulfate or sodium dodecyl sulfate.

Also provided herein is a composition or kit comprising a first nucleic acid probe attached to one or more beads, and a second nucleic acid probe attached to one or more beads, wherein said first nucleic acid probe is capable of hybridizing to a complementary region on a first target polynucleotide, and wherein said second nucleic acid probe is capable of hybridizing to a complementary region on a second target polynucleotide, wherein said first target polynucleotide comprises a first variable domain, and said second target polynucleotide comprises a second variable domain. In an embodiment, the first probe is hybridized to said first target polynucleotide, and wherein said second probe is hybridized to said second target polynucleotide.

Also provided herein is a method for identifying antibodies of interest, comprising providing primary immune cells from at least one mammalian donor; isolating single immune cells or subpopulations of immune cells from said primary immune cells in a reaction vessel; generating a plurality of recombinant fusion polynucleotides each comprising a first polynucleotide encoding a light chain variable domain polypeptide and a second polynucleotide encoding a heavy chain variable domain polypeptide, wherein said first and second polynucleotides are each from said immune cells or subpopulations of immune cells, wherein said recombinant fusion polynucleotides further comprise a linker polynucleotide linking said first and second polynucleotides; inserting at least one of each of said plurality of recombinant fusion polynucleotides into a plurality of expression vectors; expressing said expression vectors in a host cell to generate a plurality of recombinant immunoglobulins; and identifying therapeutic antibodies from said plurality of recombinant immunoglobulins that bind to an antigen of interest.

In an embodiment, the at least one mammalian donor is selected for the presence of a particular medical condition. In an embodiment, the medical condition comprises a heightened immune response to hepatitis B, rabies, tetanus toxin, varicella-zoster, cytomegalovirus, or pneumococcus. In an embodiment, the at least one mammalian donor is human. In an embodiment, the at least one said mammalian donor or cells derived from said donor were exposed to an antigen of interest before providing said primary immune cells. In an embodiment, the antigen of interest is related to a tumor or cancerous cell or tissue. In an embodiment, the antigen of interest is associated with an autoimmune disease. In an embodiment, the at least one mammalian donor was immunized against at least one antigen of interest before providing said primary immune cells. In an embodiment, the method further comprises inserting a promoter into each of the recombinant fusion polynucleotides between said first and second polynucleotides.

Also provided herein is a method for generating an immunoglobulin or T cell receptor polypeptide libraries, comprising: providing g a plurality of polynucleotide constructs, each comprising a first polynucleotide encoding a first variable domain, a second polynucleotide encoding a second variable domain, and a spacer polynucleotide linking the first and second polynucleotides, wherein each of said linked first and second variable domains are from a single cell or subpopulation of cells, and wherein said plurality of polynucleotide constructs comprises linked first and second variable domains from at least 1,000 unique cells or subpopulations of cells; for each of said plurality of polynucleotide constructs, inserting a third polynucleotide encoding a transcriptional modulator, a translational modifier, a constant region, or an immune effector into the spacer polynucleotide, thereby generating at least 1,000 unique recombinant fusion polynucleotide protein expression constructs; performing the providing and inserting step at least 1,000 times to generate at least 1,000 unique recombinant fusion polynucleotides; performing bulk expression of said at least 1,000 unique recombinant fusion polynucleotides protein expression constructs in a plurality of host cells to generate at least 1,000 unique recombinant fusion polypeptides, wherein said recombinant fusion protein polynucleotide is generated by; and purifying the at least 1,000 unique recombinant polypeptides, thereby generating an immunoglobulin or T cell receptor polypeptide library.

In an embodiment, the insertion of said third polynucleotide is performed in parallel for each of said at least 1,000 unique polynucleotide constructs. In an embodiment, at least one recombinant polypeptide from said at least 1,000 unique recombinant polypeptides binds to *Streptococcus pneumonia*, *Hemophilis influenza*, or *Klebsiella pneumonia*. In an embodiment, the variable domains are amplified from a single cell or subpopulation of cells. In an embodiment, the first variable domain is an immunoglobulin heavy chain, and said second variable domain is an immunoglobulin light chain.

In an embodiment, the first variable domain is a T cell receptor alpha and said second variable domain is a T cell receptor beta. In an embodiment, the recombinant fusion polynucleotide protein expression construct is an expression vector. In an embodiment, the expression vector is a plasmid or a phagemid. In an embodiment, the insertion of said third polynucleotide into said spacer polynucleotide comprises a method selected from the group consisting of: Gibson assembly, site-specific digestion and ligation, and targeted recombination.

Also provided herein is a composition comprising at least 1,000 unique recombinant fusion polynucleotide protein expression constructs comprising a first polynucleotide encoding a first variable domain, a second polynucleotide encoding a second variable domain, and a spacer polynucleotide linking the first and second polynucleotides, wherein said spacer polynucleotide comprises a transcriptional modulator, a translational modifier, a constant region, or an immune effector.

In an embodiment, the first variable domain and said second variable domain of each individual recombinant fusion protein expression construct from said at least 1,000 unique recombinant fusion protein expression constructs are from a single cell or subpopulation of cells. In an embodiment, the first variable domain is an immunoglobulin heavy chain, and said second variable domain is an immunoglobulin light chain. In an embodiment, the first variable domain is a T cell receptor alpha and said second variable domain is a T cell receptor beta. In an embodiment, the recombinant fusion polynucleotide expression recombinant fusion protein expression construct is an expression vector. In an embodiment, the expression vector is a plasmid or a phagemid.

Also provided herein is a method of generating a recombinant immunoglobulin library, comprising: providing primary immune cells from at least one mammalian donor; isolating single immune cells or subpopulations of immune cells from said primary immune cells in reaction vessels; generating a plurality of recombinant fusion polynucleotides each comprising a first polynucleotide encoding a heavy chain variable domain polypeptide and a second polynucleotide encoding a light chain variable domain polypeptide from each cell or subpopulation of cells, wherein said recombinant fusion polynucleotides further comprise a linker polynucleotide linking said first and second polynucleotides; inserting at least one of each of said plurality of recombinant fusion polynucleotides into a plurality of expression vectors; inserting a promoter into each of the recombinant fusion polynucleotides between said first and second polynucleotides, thereby generating a recombinant immunoglobulin encoding polynucleotide; inserting at least one of said expression vectors comprising said recombinant immunoglobulin encoding polynucleotide into a plurality of host cells; and expressing said recombinant immunoglobulin encoding polynucleotide in each of said plurality of host cells, thereby generating a recombinant immunoglobulin library.

In an embodiment, the at least one mammalian donor is selected for the presence of a particular medical condition. In an embodiment, the medical condition comprises a heightened immune response to hepatitis B, rabies, tetanus toxin, varicella-zoster, cytomegalovirus, or pneumococcus. In an embodiment, the at least one mammalian donor is human. In an embodiment, the at least one mammalian donor or cells derived from said donor was exposed to an antigen of interest before providing said primary immune cells. In an embodiment, the antigen of interest is related to a tumor or cancerous cell or tissue.

In an embodiment, the antigen of interest is associated with an autoimmune disease.

In an embodiment, the at least one mammalian donor was immunized against an antigen of interest before providing said primary immune cells. In an embodiment, the recombinant immunoglobulin library comprises at least 1,000, 10,000, 100,000, or 1,000,000 unique recombinant fusion polynucleotides. In an embodiment, the method further comprises expressing said recombinant immunoglobulin on the surface of a population of host cells, contacting said host cell population with an antigen, and selecting for a subpopulation of host cells that bind to said antigen to enrich said recombinant immunoglobulin library.

Disclosed herein are methods and compositions for generating recombinant fusion polypeptides. A first nucleic acid probe attached to a particle and a second nucleic acid probe attached to a particle are provided according to an embodiment of the invention. The first and second nucleic acid probes are attached to the same or different particles. The probes are combined with an immune cell population in a reaction vessel. The first nucleic acid probe hybridizes to a first target polynucleotide form a cell or population of cells, and the second nucleic acid probe hybridizes to a second target polynucleotide from the cell or population of cells. The immune cell population is lysed and the captured target polynucleotides are amplified and fused, thus generating the recombinant fusion polynucleotide.

Also disclosed herein is a recombinant protein expression construct useful for generating recombinant protein libraries. The construct is generated by first amplifying individual protein-coding polynucleic acid components, and then fusing those components into a single polynucleic acid construct with a polynucleic acid linker. The linker is then replaced with polynucleic acid sequences required for efficient recombinant expression of the proteins. This construct can be used to generate a single recombinant protein, but can also be used to generate a pool or library of hundreds, thousands, or millions of proteins.

Also provided herein are methods of enriching a mixture of unique fusion polypeptides.

Also provided herein are mixtures of recombinant fusion polypeptides generated by the method disclosed herein. Also provided herein is a composition comprising a pool of at least 10,000 aqueous droplets in oil solution comprising probes and target sequences for amplification and fusion.

Also disclosed herein is a recombinant protein expression construct comprised of a polynucleic acid, which is used for generating recombinant protein libraries. The construct is generated by first amplifying individual protein-coding polynucleic acid components, and then fusing those components into a single polynucleic acid construct with a polynucleic acid linker. The linker is then replaced with polynucleic acid sequences required for efficient recombinant expression of the proteins. This construct can be used to generate a single recombinant protein, but can also be used to generate a pool or library of hundreds, thousands, or millions of proteins.

In one embodiment of the invention, nucleic acid sequences encoding antibody subunits are amplified from antibody-producing cells and then fused into a single polynucleic acid construct with a polynucleic acid linker. The linker is then replaced with polynucleic acid sequences required for efficient recombinant expression of the proteins, such that an antibody library can be produced en masse.

Disclosed herein are methods and compositions for generating recombinant fusion polypeptides. A first nucleic acid probe attached to a particle and a second nucleic acid probe attached to a particle are provided according to an embodiment of the invention. The first and second nucleic acid probe are attached to the same or different particles. The probes are combined with an immune cell population in a reaction vessel. The first nucleic acid probe hybridizes to a first target polynucleotide form a cell or population of cells, and the second nucleic acid probe hybridizes to a second target polynucleotide from the cell or population of cells. The immune cell population is lysed and the captured target polynucleotides are amplified and fused, thus generating the recombinant fusion polynucleotide.

Industrial applications include protein therapeutics, molecular diagnostics, and cell therapeutics. In the area of protein therapeutics, drug developers immunize a mouse with a protein target of interest, and then extract primary B cells from that mouse. Some but not all of these B cells produce antibodies against the target of interest. In one embodiment, the current invention is used to extract the antibody-producing components of such B cells and then express the proteins in recombinant cells. Recombinant expression enables protein-screening protocols that are difficult to perform with primary B cells. In another embodiment of the invention, the constructs are used to produce polyclonal antibody libraries for targeted therapy or prophylaxis of particular pathogens.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

Figure 1A:
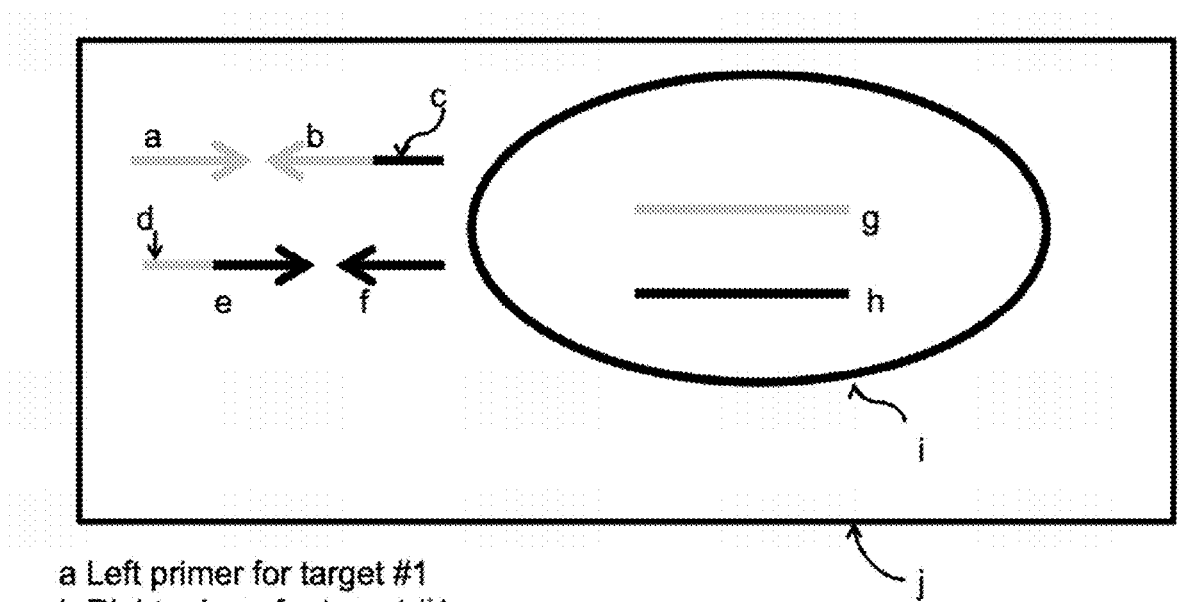
FIGS. 1A-D shows a method for generating initial linked construct using gene-targeting probes encapsulated with nucleic acids from individual gene-expressing cells inside monodisperse droplets.

The details of various embodiments of the invention are set forth in the description below. Other features, objects, and advantages of the invention will be apparent from the description and the drawings, and from the claims.

Definitions

The following terms, unless otherwise indicated, shall be understood to have the following meanings:

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "nucleic acid" refers to any materials comprised of DNA or RNA. Nucleic acids can be made synthetically or by living cells.

As used herein, the term "polynucleotide" refers to a polymeric chain of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

As used herein, the term "protein" or refers to large biological molecules, or macromolecules, consisting of one or more chains of amino acid residues. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. However, proteins may be completely artificial or recombinant, i.e., not existing naturally in a biological system.

As used herein, the term "polypeptide" refers to both naturally-occurring and non-naturally-occurring proteins, and fragments, mutants, derivatives and analogs thereof. A polypeptide may be monomeric or polymeric. A polypeptide may comprise a number of different domains each of which has one or more distinct activities.

As used herein, the term "antigen" refers to a biomolecule that binds specifically to the respective antibody. An antibody from the diverse repertoire binds a specific antigenic structure by means of its variable region interaction (CDR loops), an analogy being the fit between a lock and a key.

As used herein, the term "antibody" (i e, "immunoglobulin" (Ig)) refers to a polypeptide, at least a portion of which is encoded by at least one immunoglobulin gene, or fragment thereof, and that can bind specifically to a desired target molecule. The term includes naturally-occurring forms, as well as fragments and derivatives. The antibody recognizes a unique part of a foreign target, called an antigen. Each tip of the "Y" of an antibody contains a paratope (a structure analogous to a lock) that is specific for one particular epitope (similarly analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). The antibody consists of four polypeptide chains; two identical "heavy chains" and two identical "light chains" connected by disulfide bonds. The heavy chain is the longer than the light chain, and has two regions, the constant region and the variable region. The constant region is identical in all antibodies of the same isotype, but differs in antibodies of different isotypes. A light chain has two successive domains: one constant domain and one variable domain. The approximate length of a light chain is 211 to 217 amino acids. Each antibody contains two light chains that are always identical; only one type of light chain, κ or λ, is present per antibody in mammals.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')2, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Intracellular Antibodies: Research and Disease Applications (1998) Marasco, ed., Springer-Verlag New York, Inc.), the disclosure of which is incorporated herein by reference in its entirety).

Antibodies may be produced by any known technique, including harvest from cell culture of native B lymphocytes, harvest from culture of hybridomas, recombinant expression systems and phage display. Recombinant antibodies may also be produced by the methods as described herein.

As used herein, the term "B cell receptor" or "BCR" refers to a transmembrane receptor protein located on the outer surface of B-cells. The B cell receptor's binding moiety is composed of a membrane-bound antibody that, like all antibodies, has a unique and randomly determined antigen-binding site comprising variable domains.

As used herein, the term "region" refers to a physically contiguous portion of the primary structure of a biomolecule. In the case of proteins, a region is defined by a contiguous portion of the amino acid sequence of that protein.

As used herein, the term "domain" refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, a constant domain, a variable domain, a light chain domain, and a heavy chain domain.

As used herein, the term "variable region" or "variable domain" refers to the antigen binding region that is highly variable. This variability provides slightly different tip structures, or antigen-binding sites, allowing millions of antibodies with slightly different tip structures, or antigen-binding sites, to exist. Each of these variants can bind to a different antigen. This enormous diversity of antibodies allows the immune system to recognize an equally wide variety of antigens. The large and diverse population of antibodies is generated by random combinations of a set of gene segments that encode different antigen-binding sites (or paratopes), followed by random mutations in this area of the antibody gene, which create further diversity. T cell receptor molecules also have variable regions or variable domains.

Each antibody heavy or light chain has two regions, the constant region and the variable region. The "constant domain" is identical in all antibodies of the same isotype, but differs in antibodies of different isotypes. Isotypes of heavy chain include IGG1, IGG2, IGE, and IGA. Different isotypes have particular "effector" functions in the immune system, i.e., they activate particular biological pathways for immunity. T cell receptor molecules also have constant domains.

As used herein, the term "single chain variable fragment" (scFv) refers to a single chain antibody fragment comprised of a heavy and light chain linked by a peptide linker. In some cases scFv are expressed on the surface of an engineered cell, for the purpose of selecting particular scFv that bind to an antigen of interest.

As used herein, the term "fusion polypeptide" or "fusion protein" refers to a polypeptide comprising a polypeptide or protein fragment coupled to heterologous amino acid sequences. Fusion proteins are useful because they can be constructed to contain two or more desired functional elements from one or more proteins. A fusion protein comprises at least 10 contiguous amino acids from a polypeptide of interest, at least 20 or 30 amino acids, at least 40, 50 or 60 amino acids, or at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "transcriptional modulator" refers to any polynucleotide sequence that modulates transcription at a location in cis or trans to the transcriptional modulator. Typically, the mechanism of the transcriptional modulator is to effect binding of a transcription factor protein, or complex of proteins. Examples of transcriptional modulators include, but are not limited to, transcriptional promoters (i.e., "promoters") and transcriptional enhancers (i.e., "enhancers"). Transcriptional promoters are sequences at the 5' end of genes that modulate expression of genes. Transcriptional enhancers are polynucleotide sequences, typically in cis to the modulated gene, which effect binding of transcription factors.

As used herein, the term "translational modifier" or "translational modulator" refers to a polynucleotide or polypeptide sequence which modulates translation of a gene transcript, such as an internal ribosome entry site (IRES).

As used herein, the term "immune effector" refers to a peptide or protein sequence that selectively binds to another protein and thereby regulates immune activity Immune activity is regulated through an increase or decrease in enzyme activity, gene expression, or cell signaling, in such a way that immune cells are activated, de-activated, caused to divide, or caused not to divide. In some cases, effector molecules are secreted, such as cytokines and antibodies. In other cases, effector molecules are affixed to the surface of a cell.

As used herein, the term "protein expression construct" refers to any polynucleic acid sequence that can be used to express a recombinant protein. A protein expression construct contains, at a minimum, at least one protein-encoding region, a transcription initiation site, and a promoter sequence that modulates transcription. Many protein expression constructs are circular, such as a plasmid or a phagemid. Many protein expression constructs harbor an origin of replication (ORI) that enables self-replication of the construct inside a host cell. Other protein expression constructs are linear, and do not harbor an ORI. Some protein expression constructs are explicitly for expression in an engineered cell, whereas other protein expression constructs are for generating proteins in vitro without the benefit of cellular machinery. Examples of engineered cells include bacteria, yeast, and mammalian cells (e.g., Chinese hamster ovary or HeLa cells).

As used herein, the term "expression vector" refers to a nucleic acid molecule capable of introducing a protein expression construct into a host cell. Some expression vectors also replicate inside host cells, which increases protein expression by the protein expression construct. One type of vector is a "plasmid," which refers to a circular double stranded DNA loop into which additional DNA segments may be ligated. Other vectors include cosmids, bacterial artificial chromosomes (BAC) and yeast artificial chromosomes (YAC), fosmids, phage and phagemids. Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked Such vectors are referred to herein as "recombinant expression vectors" (or simply "expression vectors").

As used herein, the term "polynucleotide probe" (or "nucleic acid probe") refers to any nucleic acid sequence that is complementary to or binds under stringent conditions to a target nucleic acid sequence. The polynucleotide probe can be used to detect, capture, and/or amplify that target nucleic acid sequence. Polynucleotide probes include but are not limited to DNA origami structures that include 10-5000 individual oligonucleotide components. One example of a polynucleotide probe is a primer used in PCR amplification.

As used herein, the term "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

As used herein, the term "fused nucleic acid" or "recombinant fusion polynucleotide" refers to a fusion of two nucleic acid sequences into a single contiguous nucleic acid molecule. Fusion can be achieved through molecular methods that fuse nucleic acids, such as overlap extension PCR or ligation.

As used herein, the term "reaction vessel" refers to any entity that provides physical separation of a reaction into separate compartments. The reaction vessel may be used, for example, for screening or performing reactions a particular cell, cell subpopulation, or nucleic acid target to the exclusion of others. Reaction vessels may be comprised of a plastic compartment, microfluidic chamber, or a droplet, e.g. of an aqueous reaction solution.

As used herein, the term "surfactant" refers to compounds that lower the surface tension (or interfacial tension) between two liquids or between a liquid and a solid. Surfactants are typically organic compounds that are amphiphilic, meaning they contain both hydrophobic groups (their tails) and hydrophilic groups (their heads). Therefore, a surfactant contains both a water insoluble (or oil soluble) component and a water soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase. Surfactants may act as detergents, wetting agents, emulsifiers, foaming agents, and dispersants.

As used herein, the term "aqueous" refers to a solution containing water, typically as a solvent or medium.

As used herein, the term "oil" refers to any neutral, nonpolar chemical substance that is a viscous liquid at ambient temperatures and is both hydrophobic (immiscible with water, literally "water fearing") and lipophilic (miscible with other oils, literally "fat loving").

As used herein, the term "droplet" refers to a small quantity of liquid. Droplets are typically spherical, but may be comprised of cylindrical slugs that span the full diameter of a microfluidic channel. Droplets may form in air, oil, or aqueous solutions, depending on their composition of matter and the method of formation. Droplets occur in both monodisperse and polydisperse populations.

As used herein, the term "monodisperse" refers to a property of components characterized by uniform or nearly uniform size. For example, monodisperse droplets typically require size dispersity <5% for >90% of the droplets in a mixture. In many cases, monodisperse droplet populations are more stable than droplet populations that are not monodisperse, i.e., polydisperse droplet populations. In some embodiments, generation of monodisperse droplets requires some kind of controlled microfluidic device.

As used herein, the term "cell" refers to the smallest unit of an organism that can independently replicate. Cells are typically microscopic and have a cytoplasm and a nucleus enclosed in a membrane, either from either a single cell organism or derived from a multicellular organism.

As used herein, the term "cell population" or "cell subpopulation" refers to at least two cells of similar kind or classification. For example, a cell subpopulation may be two cells separated from a cell population by encapsulating the two cells in a droplet.

As used herein, the term "lysis" refers to the process of breaking the cell membrane of a cell or cells through physical or chemical means. Lysis may be achieved through a chemical surfactant such as Triton X-100, an alkaline lysis buffer, heat, electrical currents, or physical disruption.

As used herein, the term "DNA origami" refers to the nanoscale folding of DNA to create arbitrary two and three dimensional shapes at the nanoscale. The specificity of the interactions between complementary base pairs make DNA a useful construction material, through design of its base sequences. DNA origami can be polynucleotide probes folded into particles.

As used herein, the term "particle" refers to any solid substance that is added to a complex solution of biological material (i.e., a protein or a polynucleic acid) to capture and then physically isolate a target biological material. Particles may be objects such as microscopic beads made of materials such as latex, glass, or silica, ranging in size from 0.1 micron to 1 mm Particles can also refer to nanoscale-folded DNA from DNA origami.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Methods for Isolating Single Cells and Target Polynucleotides

In some embodiments, a single cell or alternatively subpopulation of cells is isolated to capture DNA or RNA from each cell or subpopulation of cells. In one embodiment, the cells are from a heterogeneous pool of T or B cells. In some embodiments, the cells are primary B cells or T cells. In some embodiments, the cells are provided from a single person.

In some embodiments, a microfluidic device is used to generate single cell emulsion droplets. The microfluidic device ejects single cells in aqueous reaction buffer into a hydrophobic oil mixture. The device can create thousands of emulsion microdroplets per minute. After the emulsion microdroplets are created, the device ejects the emulsion mixture into a trough. The mixture can be pipetted or collected into a standard reaction tube for thermocycling.

Custom microfluidics devices for single-cell analysis are routinely manufactured in academic and commercial laboratories (Kintses et al., 2010 Current Opinion in Chemical Biology 14:548-555). For example, chips may be fabricated from polydimethylsiloxane (PDMS), plastic, glass, or quartz. In some embodiments, fluid moves through the chips through the action of a pressure or syringe pump. Single cells can even be manipulated on programmable microfluidic chips using a custom dielectrophoresis device (Hunt et al., 2008 Lab Chip 8:81-87). In one embodiment, a pressure-based PDMS chip comprised of flow focusing geometry manufactured with soft lithographic technology is used (Dolomite Microfluidics (Royston, UK)) (Anna et al., 2003 Applied Physics Letters 82:364-366). The stock design can typically generate 10,000 aqueous-in-oil monodisperse microdroplets per second at size ranges from 10-150 μm in diameter. In some embodiments, the hydrophobic phase will consist of fluorinated oil containing an ammonium salt of carboxy-perfluoropolyether, which ensures optimal conditions for molecular biology and decreases the probability of droplet coalescence (Johnston et al., 1996 Science 271:624-626). To measure periodicity of cell and droplet flow, images are recorded at 50,000 frames per second using standard techniques, such as a Phantom V7 camera or Fastec InLine (Abate et al., 2009 Lab Chip 9:2628-31).

The microfluidic system can optimize microdroplet size, input cell density, chip design, and cell loading parameters such that greater than 98% of droplets contain a single cell. There are three common methods for achieving such statistics: (i) extreme dilution of the cell solution; (ii) fluorescent selection of droplets containing single cells; and (iii) The microfluidic device uses extreme cell dilution to control the multi-hit rate and fluorescent cell sorting to reduce the negative rate.

In some embodiments, input cell flow is aligned with droplet formation periodicity, such that greater than 98% of droplets contain a single cell (Edd et al., 2008 Lab Chip 8:1262-1264; Abate et al., 2009 Lab Chip 9:2628-31). In these microfluidic devices, a high-density suspension of cells is forced through a high aspect-ratio channel, such that the cell diameter is a large fraction of the channel's width. The chip is designed with a 27 μm×52 μm rectangular microchannel that flows cells into microdroplets at >10 μL/min (Edd et al., 2008 Lab Chip 8:1262-1264). A number of input channel widths and flow rates are tested to arrive at an optimal solution.

In certain embodiments of the invention, microfluidic chips are used to isolate 10, 100, 1000, 10,000, 100,000, 1 million, or 1 billion single cells from a heterogeneous pool of T or B cells. In some embodiments, the methods of the invention use single cells in reaction containers, rather than emulsion droplets. Examples of such reaction containers include 96 well plates, 0.2 mL tubes, 0.5 mL tubes, 1.5 mL tubes, 384-well plates, 1536-well plates, etc.

In some embodiments of the invention, cells are encapsulated with PCR reagents. The PCR reagent mixture is specifically designed to lyse the cells, thus releasing DNA or RNA targets of interest. The PCR reagents then amplify a plurality of the DNA or RNA targets of interest. In some embodiments of the invention, the PCR products are linked heavy and light chain immunoglobulin variable regions. In some embodiments of the invention, the PCR products are polynucleotides that encode scFv polypeptides.

In some embodiments of the invention, single cells are encapsulated into droplets with beads comprising bound polynucleic acid probes with sequences that are complementary to polynucleic acid targets of interest in the single cells. In certain embodiments, the probes are 20, 30, 40, 50, 60, 70, 80, 90, 100, 110, 120, or 130 nucleotides in length. The probes are RNA, DNA, locked nucleic acid (LNA), peptide nucleic acid (PNA), glycol nucleic acid (GNA), or any nucleic acid analogue. The polynucleic acid targets are either DNA or RNA. In some embodiments of the invention, the polynucleic acid probes target the constant region of T cell receptor or immunoglobulin. In some embodiments, the polynucleic acid probes target the constant region of IgK or IgG. The reagent mixture present in these embodiments comprising beads is specifically designed to both lyse the cells and encourage polynucleic acid hybridization, thus allowing the beads to capture DNA or RNA targets of interest.

In certain embodiments, polynucleic acid probes for both heavy and light chain immunoglobulin are bound to beads. In other embodiments, probes for heavy chain are bound to one pool of beads, and probes for light chain are bound to a second pool of beads, and then both pools of beads are encapsulated into droplets with single cells. In some embodiments, 5'-amino-modified polynucleic acid probes are bound to carboxylic acid beads using 2-(N-morpholino) ethane sulfonic acid (MES) buffer (Kojima et al., 2005, Nucleic Acids Research 33:e150). In other embodiments, biotinylated polynucleic acid probes are bound to streptavidin-coated beads.

In some embodiments, the methods of the invention use single cells in reaction containers, rather than emulsion droplets. Examples of such reaction containers include 96 well plates, 0.2 mL tubes, 0.5 mL tubes, 1.5 mL tubes, 384-well plates, 1536-well plates, etc. A variety of other designs of microfluidic chips are also used to isolate single cells (Marcus et al., 2006, Anal Chem 78:3084-3089).

In some embodiments, the cell or subpopulation of cells is added to a reaction container along with beads comprising bound polynucleic acid probes and a lysis buffer. The lysis buffer lyses the cells to allow the polynucleic acid probes to bind to the polynucleic acid targets of interest from the cell or cells. The beads hybridized to the polynucleic acid targets are isolated from the lysis buffer, as single beads or subpopulations of beads into reaction vessels, and are contacted with a PCR mix to allow amplification and or fusion of the polynucleic acid targets.

In certain embodiments of the invention, the aqueous phase of the droplet emulsions containing beads and their bound targets is recovered using a solvent such as ethyl ether. The beads are isolated into emulsions with a PCR mix, such that, on average, single beads are isolated into single emulsion microdroplets (DeKosky et al., 2015, Nat Med 21:86-91). Monodisperse emulsions can be formed on a microfluidic chip, or polydisperse emulsions can be formed using a machine such as the IKA Utra-Turrax Tube Drive system. The PCR reagents amplify a plurality of the DNA or RNA targets of interest. In some embodiments of the invention, the PCR products are linked heavy and light chain immunoglobulin variable regions. In some embodiments of the invention, the PCR products are scFv.

In certain embodiments of the invention, amplified libraries of linked variable region subunits are then converted into protein expression libraries using methods for ligation or Gibson assembly. In certain embodiments of the invention, the protein expression libraries are expressed in a recombinant protein production system such as yeast or mammalian cells.

Methods for Amplifying and Linking Variable Regions

PCR is used to amplify many kinds of sequences, including but not limited to SNPs, short tandem repeats (STRs), variable protein domains, methylated regions, and intergenic regions. Methods for overlap extension PCR are used to create fusion amplicon products of several independent genomic loci in a single tube reaction. Methods to amplify and link variable regions are disclosed in Johnson et al., 2005 Genome Research 15:1315-24; U.S. Pat. No. 7,749,697; PCT Publication WO 2012/083225; and PCT Publication WO 2013/096643, each of which is incorporated herein by reference in its entirety.

In some embodiments, at least two nucleic acid target sequences (e.g., first and second nucleic acid target sequences, or first and second loci) are chosen in the cell and designated as target loci. Forward and backward primers are designed for each of the two nucleic acid target sequences, and the primers are used to amplify the target sequences. "Minor" amplicons are generated by amplifying the two nucleic acid target sequences separately, and then fused by amplification to create a fusion amplicon, also known as a "major" amplicon. In one embodiment, a "minor" amplicon is a nucleic acid sequence amplified from a target genomic loci, and a "major" amplicon is a fusion complex generated from sequences amplified between multiple genomic loci, e.g., a recombinant fusion nucleotide.

The method uses "inner" primers (i.e., the reverse primer for the first locus and the forward primer for the second locus) comprising of one domain that hybridizes with a minor amplicon and a second domain that hybridizes with a second minor amplicon. "Inner" primers are a limiting reagent, such that during the exponential phase of PCR, inner primers are exhausted, driving overlapping domains in the minor amplicons to anneal and create major amplicons.

PCR primers are designed against targets of interest using standard parameters, i.e., melting temperature (Tm) of approximately 55-65° C., and with a length 20-50 nucleotides. The primers are used with standard PCR conditions, for example, 1 mM Tris-HCl pH 8.3, 5 mM potassium chloride, 0.15 mM magnesium chloride, 0.2-2 µM primers, 200 µM dNTPs, and a thermostable DNA polymerase. Many commercial kits are available to perform PCR, such as Platinum Taq (Life Technologies), Amplitaq Gold (Life Technologies), Titanium Taq (Clontech), Phusion polymerase (Finnzymes), HotStartTaq Plus (Qiagen). Any standard thermostable DNA polymerase can be used for this step, such as Taq polymerase or the Stoffel fragment.

In one embodiment, a set of nucleic acid probes (or primers) are used to amplify a first target nucleic acid sequence and a second target nucleic acid sequence to form a fusion complex (FIGS. 1A-D). As shown in FIG. 1A, the first probe includes a sequence that is complementary to a first target nucleic acid sequence (e.g., the 5' end of the first target nucleic acid sequence). The second probe includes a sequence that is complementary to the first target nucleic acid sequence (e.g., the 3' end of the first target nucleic acid sequence) and a second sequence that is complementary to an exogenous sequence. In some embodiments, the exogenous sequence is a non-human nucleic acid sequence and is not complementary to either of the target nucleic acid sequences. For example, the exogenous sequence might be a polynucleotide sequence that encodes a polypeptide sequence rich in Ser and Gly amino acids, which links heavy and light chain variable regions in an scFv (see, e.g., PCT/US 1992/001478). The first and second probes are the forward primer and reverse primer for the first target nucleic acid sequence.

As shown in FIG. 1A, the third probe includes a sequence that is complementary to the portion of the second probe that is complementary to the exogenous sequence and a sequence that is complementary to the second target nucleic acid sequence (e.g., the 5' end of the second target nucleic acid sequence). The fourth probe includes a sequence that is complementary to the second target nucleic acid sequence (e.g., the 3' end of the second target nucleic acid sequence). The third probe and the fourth probe are the forward and reverse primers for the second target nucleic acid sequence.

The second and third probes are also called the "inner" primers of the reaction (i.e., the reverse primer for the first locus and the forward primer for the second locus) and are limiting in concentration, (e.g., 0.01 µM for the inner primers and 0.1 µM for all other primers). This will drive amplification of the major amplicon preferentially over the minor amplicons. The first and fourth probes are called the "outer" primers.

Figure 1B:
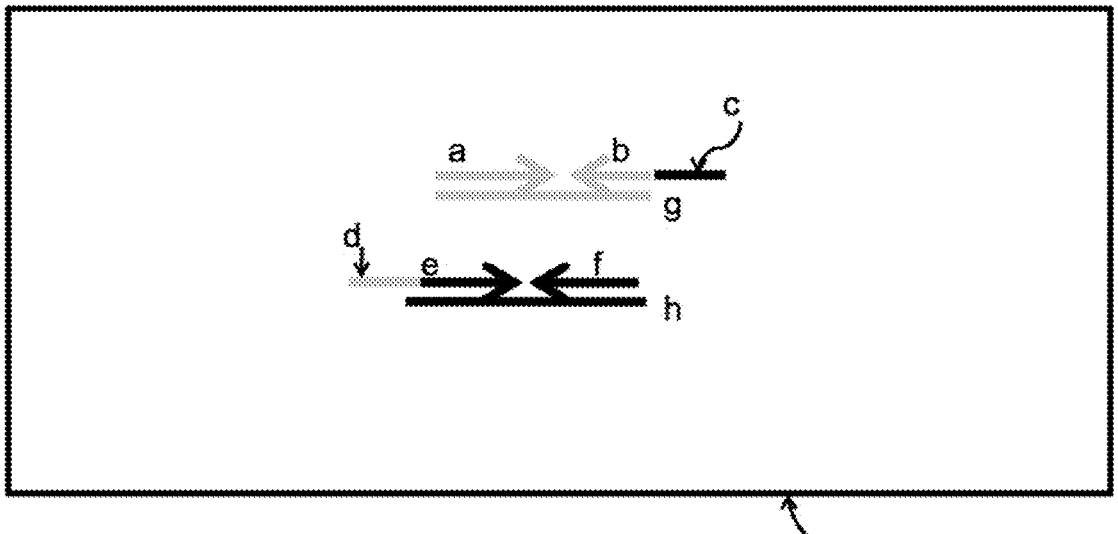
Figure 1C:
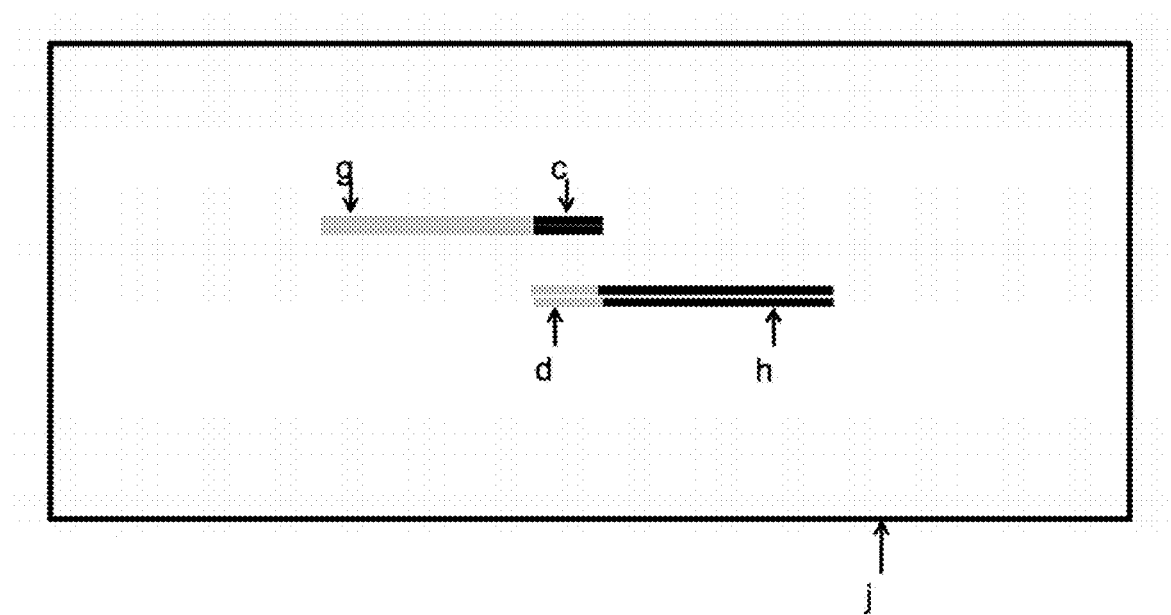
Figure 1D:
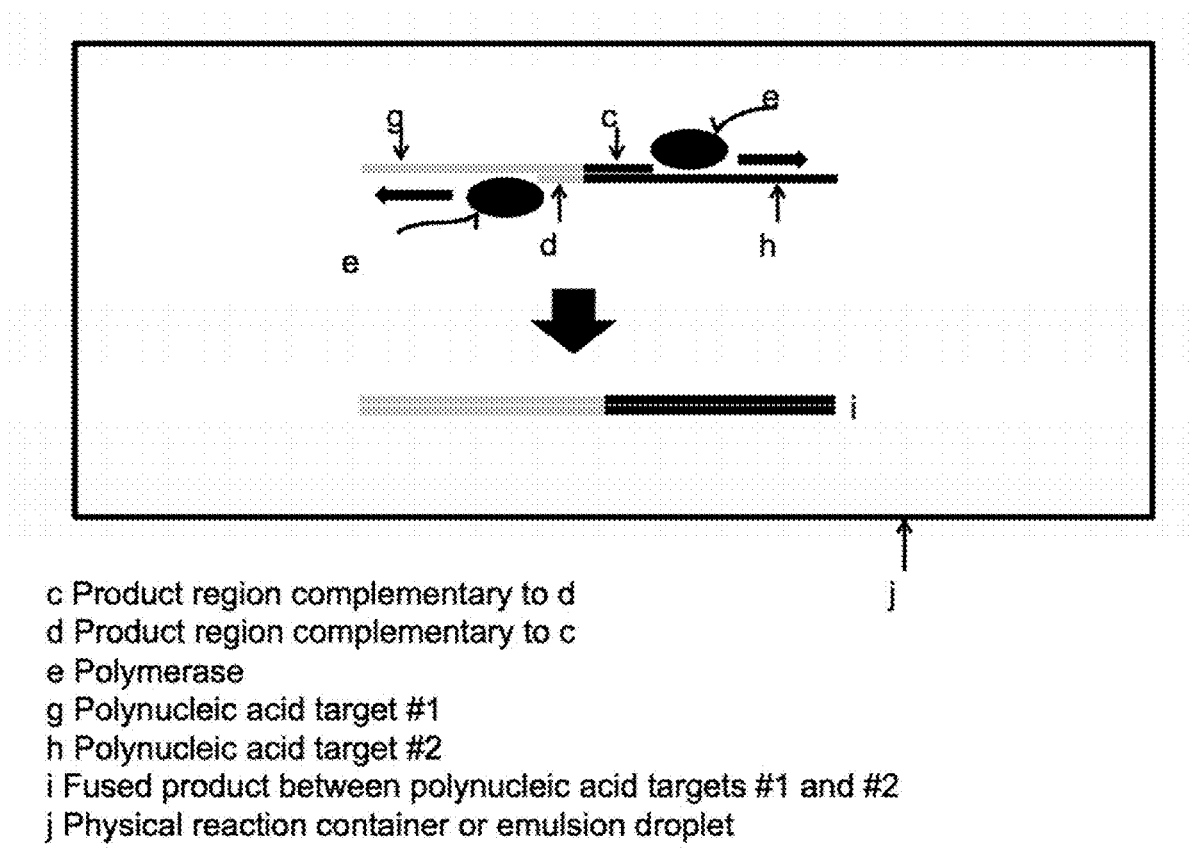

As shown in FIGS. 1B and 1C, the first and second nucleic acid sequences are amplified independently, such that the first nucleic acid sequence is amplified using the first probe and the second probe, and the second nucleic acid sequence is amplified using the third probe and the fourth probe. Next, a fusion complex is generated by hybridizing the complementary sequence regions of the amplified first and second nucleic acid sequences and amplifying the hybridized sequences using the first and fourth probes (FIG. 1D). This is called overlap extension PCR amplification.

During overlap extension PCR amplification, the complementary sequence regions of the amplified first and second nucleic acid sequences act as primers for extension on both strands and in each direction by DNA polymerase molecules. In subsequent PCR cycles, the outer primers prime the full fused sequence such that the fused complex is duplicated by DNA polymerase. This method produces a plurality of fusion complexes. In some embodiments, the fusion complexes comprise a heavy chain and light chain variable region from the same cell or subpopulation of cells. In some embodiments, the fusion complex is used as an scFv insert.

Methods for Engineering Polynucleic Acid Protein Expression Constructs

Figure 2:
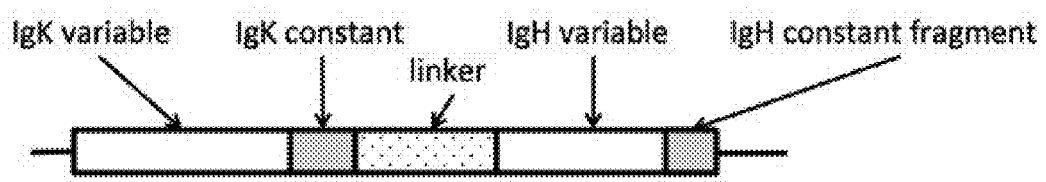
FIG. 2 shows an scFv expression construct comprising a linked heavy chain and light chain variable domain encoding polynucleotide from a single cell.

In some embodiments, variable regions for heavy and light chain immunoglobulin are linked and amplified, or amplified and linked, to form a plurality of polynucleic acid constructs comprising a heavy and light chain Ig variable region connected by a linker polynucleotide, to form, e.g., an scFv encoding polynucleotide. (FIG. 2). In other embodiments, variable regions for T cell receptor alpha and beta are linked and amplified, or amplified and linked, to form a plurality of polynucleic acid constructs comprising an alpha and beta T cell receptor connected by a linker polynucleotide. In certain embodiments, the variable T cell receptor sequences or Ig sequences are amplified from naturally occurring genes, especially from single cells or clonal populations of cells. In other embodiments, variable T cell receptor sequences or Ig sequences are generated artificially using gene synthesis methodologies (Kosuri & Church, 2014, Nat Methods 11:499-507). In other embodiments, the library of linked complexes is generated from completely artificial sequences, i.e., a large diversity (e.g., ~$10^{12}$ unique sequences) library of randomized DNA sequences. In certain embodiments, the linked variable regions form an scFv that can be expressed in host prokaryotic or eukaryotic cells as a recombinant secreted or surface protein. In some embodiments, recombinant scFv are expressed using ribosome display (Hanes et al., 1997, PNAS 94: 4937-42) or mRNA display (Mattheakis et al., 1994, Affymax Research Institute 91:9022-6). In other embodiments of the current invention, linked variable region subunit polynucleotide constructs are never expressed as protein, and instead serve as an intermediary polynucleotide construct or library of constructs for subsequent generation of a polynucleotide construct or library of polynucleotide constructs that encode a full-length protein or library of proteins. In certain embodiments of the invention, the libraries are comprised of one, tens, hundreds, thousands, millions, or billions of unique sequences.

Figure 3:
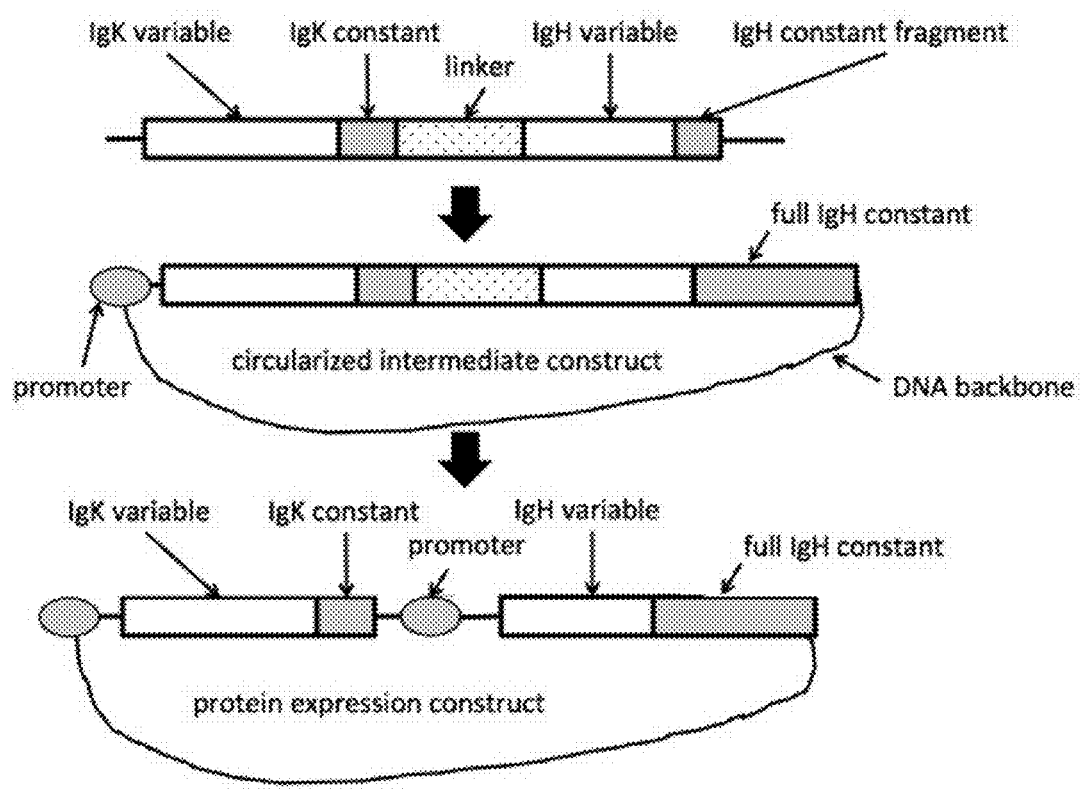
FIG. 3 shows a method for generating an immunoglobulin expression construct from initial linked variable domain encoding polynucleotides from a single cell.

In some embodiments of the invention, the polynucleotide construct comprising the variable domain encoding polynucleotides from a single isolated cell connected by a linker polynucleotide in a single polynucleotide is circularized. (see FIG. 3, top and middle panel). For example, if the original construct is part of a library of more than one constructs, then circularization is beneficial to retain any pairing between polynucleotide subunits amplified to form the initial linked polynucleotide sequence. In one embodiment, a library of scFv is created from thousands of single B cells. It is often desirable to insert into the scFv linker polynucleotide or replace at least a part of the scFv linker polynucleotide with a promoter and other sequence elements that are important to convert the scFv library into a library of full-length antibodies using DNA engineering methods described below. If the linear scFv were cleaved at the linker en masse, the resulting library would no longer retain the native heavy and light chain variable region pairings of the original isolated cells. Thus, it is important to circularize the construct before insertion of a promoter or other sequence elements into the construct between the variable domain encoding sequences to maintain the pairing of the original isolated cells (FIG. 3).

In some embodiments, the scFv library is circularized by first using restriction endonucleases to digest a plasmid and the scFv constructs, followed by ligation of the scFv constructs into the plasmid. In other embodiments, a linear DNA construct is used instead of a plasmid. Restriction enzymes cut DNA at or near specific recognition nucleotide sequences known as restriction sites. Restriction endonucleases such as EcoRI and NotI are routinely used in molecular biology and available commercially from vendors such as New England Biolabs. In some embodiments of the invention, DNA ligase is then used to ligate the "sticky ends" from a plasmid with the sticky ends from the scFv library. In other embodiments of the invention, a T4 DNA ligase is used to circularize the scFv directly, or by inserting the scFv library into a linear DNA with blunt ends. In other embodiments of the invention, Gibson assembly is used to circularize the scFv library (Gibson et al., 2008, Science 319: 1215-20). In the process of Gibson assembly, at least two DNA constructs with overlapping ends are mixed in a reaction tube. A 5' exonuclease enzyme is used to chew back 5' ends from the constructs. The constructs then anneal and a DNA polymerase is used to extend the 3' ends of the DNA. Finally, a DNA ligase seals the remaining nicks in the double-stranded DNA. In other embodiments of the invention, DNA engineering is achieved through homologous recombination or non-homologous end joining.

In some embodiments of the invention, a circularized plasmid is transformed into bacteria. In some embodiments of the invention, the plasmid confers resistance to an antibiotic, and selection of the transformed bacteria with media containing antibiotic is used to generate a plurality of bacterial clones that contain the plasmid. After using such DNA engineering methods to alter the DNA, DNA sequencing is used to verify the construct or library of constructs. DNA sequencing is performed using massively parallel methods from vendors such as Illumina, or using single-clone sequencing methods such as Sanger sequencing from vendors such as Applied Biosystems.

In certain embodiments, DNA engineering methods, such as restriction endonucleases and Gibson assembly, as described above, are also used to insert certain polynucleic acid sequences into the linked, circularized polynucleic acid construct. In certain embodiments, the inserted sequence replaces part or all of the linker polynucleotide connecting the two variable domain encoding polynucleotide sequences. In certain embodiments of the invention, the inserted polynucleic acid is necessary or beneficial for transcription of the recombinant construct (e.g., a promoter or enhancer) in recombinant cells (see FIG. 3, bottom panel). In other embodiments of the invention, the inserted polynucleic acid encodes protein segments important for a therapeutic modality, e.g., immune effector sequences. These protein-coding segments are inserted into the initial construct in frame, such that the resulting polynucleotide construct produces a protein or proteins in-frame with the original construct. In certain embodiments of the invention, the inserted components are amplified from genomic DNA or mRNA. In other embodiments of the invention, the inserted components are synthesized in vitro using DNA oligonucleotides as starting material. In certain embodiments of the invention, the scFv libraries are comprised of tens, hundreds, thousands, millions, or billions of unique sequences, and DNA engineering methods are used to insert polynucleic acid sequences into the initial linked polynucleic acid construct en masse in a single reaction tube. After using such DNA engineering methods to alter the DNA, DNA sequencing is used to verify the construct or library of constructs. DNA sequencing is performed using massively parallel methods from vendors such as Illumina, or using single-clone sequencing methods such as Sanger sequencing from vendors such as Applied Biosystems.

In some embodiments, the method of generation of the library of immunoglobulins or T cell receptors is done without affinity selection. The high throughput methods described herein can be used to generate an antigen binding protein (e.g., immunoglobulin) library comprising at least 1,000, 10,000, 100,000 or more unique antigen binding proteins, each having a variable sequences paired from a single isolated immune sell (i.e., a cognate pair). Affinity selection may also be used as an additional step to generate a refined antigen binding protein library.

Methods for Recombinant Protein Expression

Recombinant scFv are routinely expressed in phage, in a process called phage display (Smith, 1985, Science 228:1315-17; McCafferty et al., 1990, Nature 348:552-554). Phage display is a common laboratory technique for the study of protein-protein, protein-peptide, and protein-DNA interactions that uses bacteriophages (viruses that infect bacteria) to connect proteins with the genetic information that encodes them. Applications of phage display technology include determination of interaction partners of a protein (which would be used as the immobilized phage "bait" with a DNA library consisting of all coding sequences of a cell, tissue or organism) so that the function or the mechanism of the function of that protein may be determined. Phage display is also a widely used method for in vitro protein evolution (also called protein engineering). As such, phage display is a useful tool in drug discovery. It is used for finding new ligands (enzyme inhibitors, receptor agonists and antagonists) to target proteins (Lunder et al., 2005, J Lipid Research 46:1512-1516; Bratkovic et al., 2005, Biochem Biophys Res Commun 332:897-903). The technique is also used to determine tumour antigens (for use in diagnosis and therapeutic targeting) and in searching for protein-DNA interactions using specially-constructed DNA libraries with randomized segments (Hufton et al., 1999, J. Immunol Methods 231: 39-51; Gommans et al., 2005, J Mol Biol 354:507-519). Libraries of engineered phage are comprised of hundreds, thousands, millions, or billions of unique scFv sequences. Large library diversity enables screening for scFv with affinity to an antigen of interest in a massively parallel fashion.

Recombinant scFv are routinely expressed on the surface of eukaryotic cells such as mammalian cells and yeast. The advantage of cell surface display is the use of quantitative flow cytometric sorting and analysis to identify high-affinity interactions and normalize for antibody protein expression Minimally, polynucleotide expression constructs for scFv surface expression include polynucleotide sequences for a transcriptional promoter, a heavy chain variable region sequence, a polypeptide linker sequence, and a light chain variable region sequence. Yeast display is similar to phage display in that a recombinant scFv is engineered into a polynucleotide expression construct and then trafficked to the surface of the yeast, using a peptide trafficking signal such as Aga2 (Boder & Wittrup, 1997, Nat Biotech, 15:553-57). Commonly used yeast strains for recombinant protein expression include *Pichia pastoris* and *Saccharomyces cerevisiae*.

In some embodiments, yeast display is used for the study of protein-protein, protein-peptide, and protein-DNA interactions. Libraries of engineered yeast are comprised of hundreds, thousands, millions, or billions of unique scFv sequences. Large library diversity enables screening for scFv with affinity to an antigen of interest in a massively parallel fashion (Dangaj et al., 2013, Cancer Res 73:4820-4829). In other embodiments, mammalian cells are used for surface expression of scFv instead of yeast (Ho et al., 2006, PNAS 103:25). In certain embodiments, mammalian cell surface expression occurs by fusing the scFv to CCR5 protein, or the platelet-derived growth factor (PDGF) (Urban et al., 2005, Nucleic Acids Research 33:e35; Wolkowicz et al., 2005, J Biol Chem 280:15195-15201). Mammalian cells for recombinant protein expression include Chinese hamster ovary (CHO) cells (Anderson et al., 2004, Curr Opin Biotechnol 15:456-462). Recombinant DNA is introduced into the mammalian cell genome using a retrovirus, or introduced transiently into the mammalian cells using a self-replicating plasmid.

In certain embodiments of the sequence, polynucleotide complexes comprised of linked heavy and light chain Ig (e.g., scFv) are converted to full-length antibody proteins for downstream applications, such as antibody therapeutics. Such applications require additional portions of the antibody sequences that are not present in scFv, and which would be difficult to amplify from single cells. Additionally, in certain embodiments, because antibodies are comprised of protein product from two genes (heavy and light chain Ig), a full-length antibody expression construct requires two promoters, i.e., one promoter each for heavy and light chain (see, e.g., FIG. 3, bottom panel). In other embodiments, the scFv linker is replaced with an internal ribosome entry site (IRES), which enables separate expression of heavy and light chain Ig. Cell-free systems like ribosome display can produce large ($\sim 10^{13}$ to $10^{14}$ unique antibodies) diversity libraries of antibodies (Hanes & Pluckthun, 1997, PNAS 94:4937-4942). Though cell-free systems are useful for many applications, problems with protein folding, posttranslational modifications, and codon usage limit the utility of such methods for producing fully functional therapeutic antibodies. In certain embodiments of the invention, polynucleotide complexes comprised of linked heavy and light chain Ig are converted into full-length expression constructs using the methods described above. In other embodiments of the invention, polynucleotide complexes comprised of linked T cell receptor subunits are converted into full-length expression constructs using the methods above. In certain embodiments of the invention, the full-length expression constructs are used to induce recombinant protein expression in cells such as bacteria, yeast, or mammalian cells. In certain embodiments, the library of full-length expression constructs is comprised of tens, hundreds, thousands, millions, or billions of different proteins. In certain embodiments of the invention, the full library of full-length constructs is introduced into recombinant protein-producing cells en masse, to produce a cell library comprised of tens, hundreds, thousands, millions, or billions of different clones that can be used to produce a protein library comprised of tens, hundreds, thousands, millions, or billions of different proteins.

Protocols for full-length antibody expression in mammalian cells are well understood, with the first commercial monoclonal antibodies produced in CHO reaching the market in 1997 (Rituxan). Minimally, a full-length antibody polynucleotide expression construct is comprised of polynucleotide sequences encoding a full-length heavy chain protein, a promoter for the heavy chain, a full-length light chain protein, and a promoter for the light chain. Promoters for antibody expression include human cytomegalovirus (hCMV). Mammalian cells are transfected with the antibody expression constructs using methods such as electroporation, calcium phosphate precipitation, lipofection, and retroviral transfection. These methods are used to introduce a library of full-length constructs into recombinant protein-producing cells en masse, to produce a cell library comprised of tens, hundreds, thousands, millions, or billions of different clones that can be used to produce a protein library comprised of tens, hundreds, thousands, millions, or billions of different proteins. The expression vectors may include resistance markers against compounds such as hygromycin, which can be used to select against cells that have not been successfully transfected with the recombinant expression vector. CHO cultures are typically maintained in shake flasks at 37° C. in 8% $CO_2$, using media available commercially from suppliers such as GIBCO and HyClone. In certain embodiments, the host cells are deficient in metabolic enzymes such as dihydrofolate reductase (DHFR). Cells that are deficient in DHFR are proline-required auxotrophs, so transfecting DHFR-deficient CHO cells with vectors that contain DHFR and then growing the transfected cells in proline-deficient medium can help select clones that express the full-length antibodies. Thus, both negative selection (e.g., hygromycin) and positive selection (e.g., rescued DHFR deficiency) can be used to generate large libraries of mammalian cell clones that express full-length antibodies. In other embodiments, stable transfectants are generated using site-specific recombination, for example, using the Cre/loxP engineering system (Kameyama et al., 2010, Biotechnol Bioeng 105:1106-1114; Wiberg et al., 2006, Biotech Bioeng 94:396-405). Such methods enable more predictable protein expression levels across large libraries of mammalian cell clones. In other embodiments, an artificial chromosome expression (ACE) system is used to express recombinant proteins. The ACE system consists of a mammalian-based artificial chromosome known as Platform ACE, an ACE targeting vector (ATV) and a mutant λ, integrase (ACE integrase) for targeted recombination (Kennard et al., 2009, Biotechnol Bioeng 104:540-553). Platform ACE consists of mainly tandem repeated ribosomal genes and repetitive satellite sequences, which form the pericentromeric heterochromatin. It also has natural centromeres and telomeres to enable DNA replication without the need of integration into host cell genome, reducing the probability of chromosomal aberration and clonal heterogeneity.

In other embodiments of the invention, yeast are used to produce recombinant protein. Yeast strains commonly used for recombinant protein production include *Pichia pastoris* and *Saccharomyces cerevisiae*. In certain embodiments, production of proteins requires post-translational protein modifications that do not occur naturally in wild type yeast. In such cases, it is useful to use glyco-engineered yeast, for example, the GlycoSwitch technology, which is a family of *Pichia* strains that are engineered to have post-translational glycosylation that is more "humanlike", for example, as Gal(2) GlcNAc(2)Man(3)GlcNAc(2)N-glycans (Jacobs et al., 2009, Nat Protoc, 4:58-70). Yeast are routinely cultured in media such as YPD (1% yeast extract, 2% peptone, 2% dextrose), typically at 30° C. Many different vectors are commercially available, such as the pPICZ series of vectors from Life Technologies. Typically these vectors contain resistance to a chemical that can be used to negatively select un-transformed yeast, such as zeocin or kanomycin. Polynucleotide constructs or libraries of polynucleotide constructs are routinely introduced into yeast cells using an electroporator, though spheroplast generation, LiCl, and polyethylene glycol methods are also used. In certain embodiments, the AOX1 promoter is used to induce protein expression (Cregg et al., 2011, Methods in Enzymology 463:169-187). Secretion of recombinant protein is routinely directed using peptide signals such as alpha-MF at the $NH_2$ terminus of the recombinant protein. In many embodiments, it is possible to engineer yeast to generate and secrete recombinant protein at production levels as high as 10 g/L.

In certain embodiments of the invention, it is desirable to express the proteins in primary T cells, particularly for chimeric antigen receptor modified T cells (CARs). In some embodiments of the invention, the protein expression construct is subjected to in vitro transcription to produce an mRNA. These mRNA are then introduced into primary T cells using electroporation. In other embodiments of the invention, the protein expression constructs are retroviruses, which are transfected into primary T cells, incorporating the protein expression construct into the genome.

Monoclonal Antibody Drug Discovery

Antibody therapeutics are increasingly used by pharmaceutical companies to treat intractable diseases such as cancer (Carter 2006 Nature Reviews Immunology 6:343-357). However, the process of antibody drug discovery is expensive and tedious, requiring the identification of an antigen, and then the isolation and production of monoclonal antibodies with activity against the antigen. Individuals that have been exposed to disease produce antibodies against antigens associated with that disease, so it is possible mine patient immune repertoires for antibodies that could be used for pharmaceutical development. However, a functional monoclonal antibody requires both heavy and light chain immunoglobulins.

Figure 4:
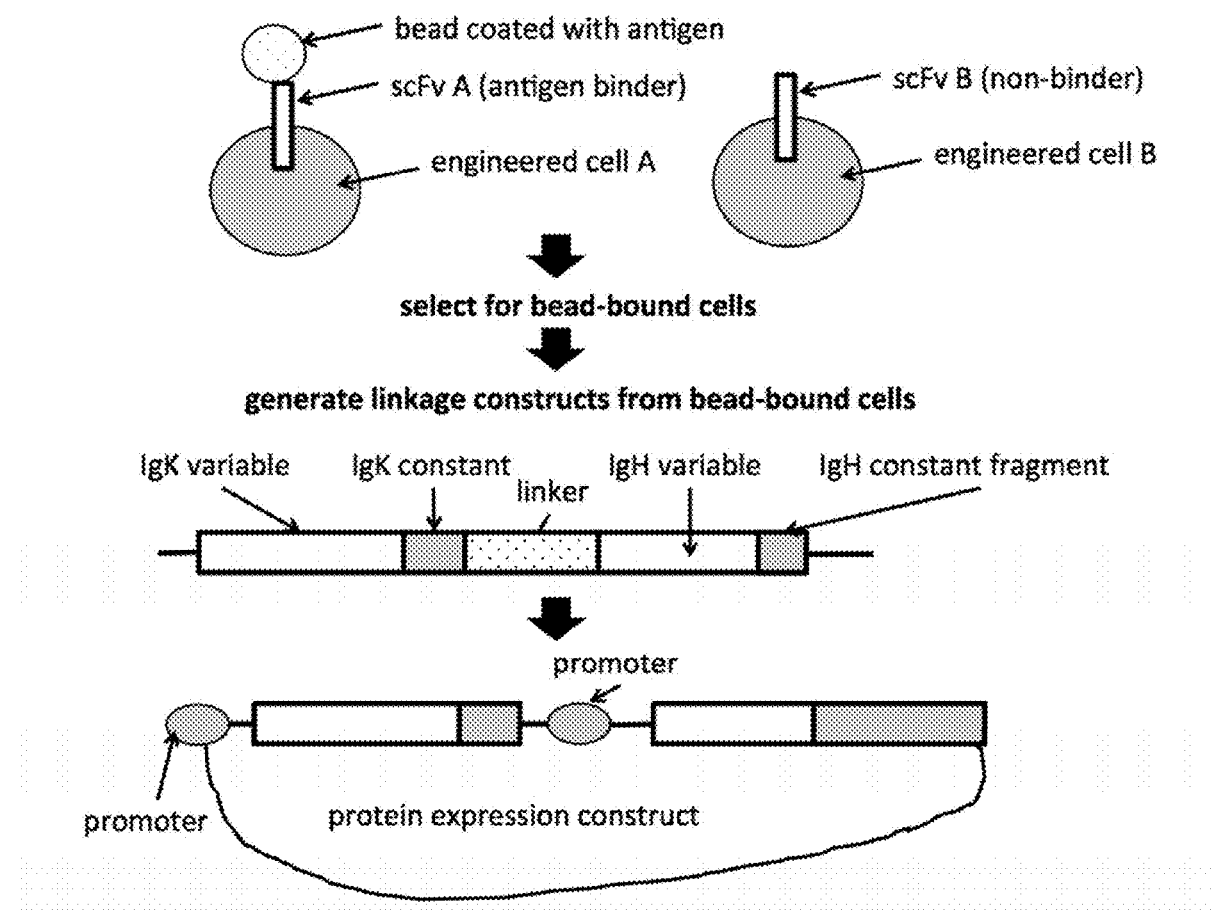
FIG. 4 shows a method for selecting libraries of cells expressing antibody fragments with affinity for an antigen of interest.

Certain embodiments of the invention require a large library of linked polynucleotide constructs comprised of variable regions from heavy and light chain Ig. In certain embodiments, the library is generated from hundreds, thousands, millions, or billions of single B cells. B cell isolation may be performed using droplet microfluidics, or isolation into physical containers such as 96-well plates. The library is either pre-enriched for a particular target of interest, or enriched through affinity screening as surface-expressed scFv (FIG. 4). The enriched library is then converted to a library of full-length antibodies by first engineering the linked polynucleotide constructs into polynucleotide constructs that encode full-length antibodies, and then screening the full-length antibodies for affinity or activity against a particular antigen. Conversion to full-length antibodies is particularly useful, because many scFv with affinity against an antigen do not have affinity against antigens when converted to full-length antibodies. In some embodiments, the scFv DNA library is generated from primary B cells isolated from human donors. In certain embodiments, enrichment occurs by exposing human donors to a vaccine comprised of antigens from a particular pathogen, such that B cells from the human donors are enriched for antibodies against those antigens. In other embodiments, B cells are isolated from donors with a particular clinical disease, such as autoimmune disease or cancer. In other embodiments, the library of linked Ig complexes is generated from completely artificial sequences, i.e., a large $10^{12}$ diversity library of randomized DNA sequences.

In some embodiments of the invention, mice are immunized with a protein or other kind of antigen of interest. Single B cells are isolated and linked complexes of paired heavy and light chain variable regions are produced in vitro. B cell isolation may be performed using droplet microfluidics, or isolation into physical containers such as 96-well plates. In some embodiments, these libraries are expressed on the surface of engineered cells as scFv, and then the engineered cells are sorted for binding to sequence variants of the antigen of interest. In some embodiments, RNA or DNA is extracted from the sorted engineered cells, and the RNA or DNA is sequenced to determine the immunoglobulin content of the selected cells. In some embodiments, linked Ig complexes amplified from the antigen-selected engineered cells are then cloned en masse into a circular DNA construct, such as a plasmid vector, to produce a library of hundreds, thousands, or millions of circularized linked complexes. In certain embodiments, this selected library of plasmid vectors is enriched for Ig complexes with affinity toward an antigen of interest.

To study the function of these Ig complexes as full-length antibodies, the linker sequence between the heavy and light chain variable region polynucleotide sequences is then replaced with a polynucleotide sequence that encodes immunoglobulin protein subunits required for expression of the full length antibody. In some embodiments of this invention, the inserted polynucleotide sequence also includes a transcriptional promoter that drives expression of one of the Ig chains. In some embodiments of the invention, the library of protein expression constructs is then introduced into a population of host cells to produce a library of engineered cells that express a library of hundreds, thousands, or millions of recombinant proteins. The library of full-length antibodies is then analyzed to discover monoclonal antibodies that may be of use therapeutically. In certain embodiments, functional monoclonal antibodies are discovered by first isolating subpopulations of engineered cells and then screening pools for affinity against a particular antigen. Pools of engineered that show activity against an antigen are then divided into single cells, and screened again for affinity against a single antigen. Cell isolation may be performed using droplet microfluidics, or isolation into physical containers such as 96-well plates. In this way, monoclonal antibodies with affinity for antigens of interest are discovered.

Polyclonal Antibody Therapeutics

Intravenous immunoglobulin (IVIg) is a pool of proteins isolated from the plasma of thousands of donors. The US Food and Drug Administration (FDA) has approved IVIg therapy for six indications, including idiopathic (immune) thrombocytopenic purpura (ITP), Kawasaki's vasculitis, B cell chronic lymphocytic leukemia (CLL), and primary immunodeficiencies (Orange et al., 2006). Though the mechanism for autoimmune modulation is unknown, most IVIg is used as replacement therapy for patients who are deficient in antibodies (Hartung et al., 2009). IVIg sales are $7 billion worldwide and growing at 8-10% per year, due to an aging population and ever-expanding off-label modalities (Taylor & Shapiro, 2013).

Current methods for IVIg production threaten continued expansion of IVIg therapy because of supply chain risk, impurities, and batch-to-batch variability. IVIg production is highly dependent on limited human sera supply and requires investment in expensive, large-scale purification facilities. More than 90% of global supply is in the hands of only 3 companies. In 2006, demand for IVIg exceeded supply by 4%, which caused physicians to ration supply by turning away patients and administering lower doses (McGinnity, 2007). Because IVIg is purified from primary sera, protein impurities and the spectre of viral contamination are a continuing problem. Octapharma recently suffered a massive voluntary recall of its IVIg product (Octagam 5%) because of complications resulting from contamination by coagulation factor XIa (Roemisch et al., 2011). IVIg depends on antigen binding through its polyclonal variable region milieu. However, because of the vast diversity of immune repertoires in donor populations, preps always have different variable region content. A survey of anti-HAV antibody titers of IVIg preps from 30 different pools of >60,000 donors showed high variability with a CV of 33% among pools (Simon & Spath, 2003).

In one embodiment of the invention, IVIg is produced in recombinant cells rather than extracted from donor plasma. In this embodiment, primary B cells are collected from thousands of human donors. Single cells are isolated and linked complexes of paired heavy and light chain variable regions are produced in vitro. B cell isolation may be performed using droplet microfluidics, or isolation into physical containers such as 96-well plates. In some embodiments, the linked complexes are cloned en masse into a circular DNA construct, such as a plasmid vector, to produce a library of hundreds, thousands, or millions of circularized linked complexes. The linker sequence between the heavy and light chain variable region polynucleotide sequences is then replaced with a linker construct that includes a transcriptional promoter and any required portions of heavy or light chain Ig. In some embodiments of the invention, the library of protein expression constructs is then introduced into a population of cells, to produce a library of engineered cells that express a library of hundreds, thousands, or millions of antibody proteins. In some embodiments, these antibody proteins are substantially equivalent to the antibodies produced by the original primary B cells. The pool of antibody proteins is therefore used as a recombinant replacement for IVIg. In some embodiments, massively parallel DNA sequencing is used to determine the diversity of the B cells, the initial library of paired heavy and light chain Ig, the library of protein expression constructs, and/or the engineered host cells. DNA sequencing may be useful as a quality control/quality assurance step for cell banking and protein library production.

In another embodiment of the invention, patients are selected for the presence of a particular medical condition, such as exposure to a particular pathogen. These patients act as donors for B cells that are enriched for production of antibodies against that particular pathogen. Conventional IVIg producers already market conventional IVIg hyperimmunes with heightened activity against pathogens such as hepatitis B, rabies, tetanus toxin, varicella-zoster, and cytomegalovirus (CMV). In one embodiment of the invention, B cell donors are injected with a vaccine against pneumococcus. B cells are extracted from these donors and then large libraries of polynucleotide protein expression constructs are made from hundreds, thousands, or millions of single B cells. B cell isolation may be performed using droplet microfluidics, or isolation into physical containers such as 96-well plates. In certain embodiments, these protein expression constructs are introduced into engineered cells en masse and then protein libraries are produced from the engineered cells. These protein libraries may contain hundreds, thousands, or millions of individual antibodies, depending on the diversity of the starting input B cells. In some embodiments, the resulting protein libraries are used as targeted polyclonal therapeutics against particular pathogens, such as CMV. In other embodiments of the invention, cells are engineered to express surface scFv using a library of linked sequences generated from primary B cells. The scFv-expressing cells are then exposed to an antigen of interest, such as CMV antigen, to positively select for scFv with affinity for said antigen. The library of enriched cells is then used to generate a library of full-length therapeutic antibodies as described above. In some embodiments, massively parallel DNA sequencing is used to determine the diversity of the B cells, the initial library of paired heavy and light chain Ig, the library of protein expression constructs, and/or the engineered host cells. DNA sequencing may be useful as a quality control/quality assurance step for cell banking and protein library production.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1 scFv Library Generation

Methods and compositions of the invention will now be discussed relative to scFv library generation.

Preparation of Beads

2× LiCl buffer was prepared as follows: For 250 mL of 2× LiCl buffer, 10 mL of 1M Tris (pH 7.5), 31.25 mL 8M LiCl, and 1 mL of 500 mM EDTA were added to 180.25 mL molecular grade water. 2× lysis buffer was prepared as follows: For each 1 mL of 2× lysis buffer, 890 μL of 2× LiCl stock, 90 μL of molecular grade water, 10 ul of 1M DTT, and 10 μL of Tween 20 were mixed to produce 1 mL solution of 2× lysis buffer.

Biotinylated IgK and IgG probes, which bind to the IgK and IgG constant regions, respectively, were synthesized with the following sequences: SEQ ID NO: 6-7. Probes were each added to 100 μL of 2× lysis buffer to a final concentration of 10 μM.

A 1 μM solution of streptavidin magnetic beads from New England Biolabs (NEB 514205) was gently rocked at room temperature for 30 minutes. 200 μL of the streptavidin magnetic bead solution was placed into a 1.5 mL tube. A strong magnet was used to remove supernatant from the beads. The beads were then washed with 600 μL of 2× lysis buffer, followed by removal of supernatant from the beads using a strong magnet. Beads were then re-suspended in 60 μL of the 10 μM IgK and IgG probes. The bead-probe mixture was incubated at room temperature for 10 minutes. After incubation, the mixture was exposed to a magnet to remove the supernatant. The beads were then twice washed with 200 μL of 2× lysis buffer, followed by removal of the supernatant with a magnet after each wash. After washing, the beads were re-suspended in 500 μL of 2× lysis buffer (1:2.5 dilution). 5 μL of an RNase inhibitor were added to the beads (1% final RNase concentration) and the solution was gently mixed.

Capture of RNA Transcripts from Cells on Beads in Emulsions

A microfluidic system with three pressure pumps (Dolomite microfluidics) was set up and connected to a pressure source of at least 6000 mbar. One pressure pump chamber was filled with a solution of mineral oil comprising 4.5% Span-80, 0.4% Tween 80, and 0.05% Triton X-100. The second pressure chamber was filled with Dulbecco's Phosphate-Buffered Saline (DPBS). The third pressure pump chamber was filled with water. Each of the three pressure pumps was connected to a microfluidic droplet chip (Dolomite microfluidics) comprising inputs for oil and aqueous phases, a flow-focusing junction for droplet generation, and channels coated with a hydrophobic material. Primary B cells were purified using a pan-B negative selection kit (Stem Cells Inc.) and mixed with a Adalumimab-expressing Chinese hamster ovary (CHO) cell clone at 0.1% prevalence in DPBS, and then loaded into the second pressure chamber and the bead mixture described above was loaded into the third pressure chamber. The CHO line acts as a positive control, expressing the previously published monoclonal antibody sequence Adalumimab (http://www.drugbank.ca/drugs/DB00051). All three pumps were then initialized at around 50% maximum pressure. Droplet formation was normalized, and emulsions containing droplets with the bead/cell mixture were collected into PCR tubes. The tubes were then incubated at 50° C. for 30 minutes. After incubation, ethyl acetate extraction was performed. A 2:1 volume of ethyl acetate was added to each tube, transferred to a 1.5 mL tube, followed by vortexing and centrifugation at full speed for 1 minute. After centrifugation, the supernatant was removed. The process was repeated with a 1:1 volume of ethyl acetate until enough of the emulsion had broken. After ethyl acetate extraction, the tube was placed on a strong magnet for 1-2 minutes and all supernatant was removed and discarded.

Amplification of Linked Complexes from Beads in Emulsions to Form scFv Encoding Polynucleotide Beads comprising probes attached to RNA transcripts collected above were then exposed to overlap extension RT-PCR to amplify the RNA transcripts.

25 µL of the beads with bound RNA transcripts were transferred to a 1.5 mL tube, and put on a magnet, allowing removal of the supernatant. The beads were then washed with 100 µL of water, followed by removal of the supernatant. Next, single beads or subpopulations of beads were isolated into reaction chambers to amplify RNA from a single cell or subpopulation of cells. To accomplish this, the beads were re-suspended in 250 µL of cold RT-PCR mix (kits and enzymes from NEB, Thermo Fisher, and Qiagen). The RT-PCR mix consisted a final concentration of: 1x reaction buffer, 1 µM outer IgK V primer (SEQ ID NO: 8), 0.2 µm inner IgK C primer (SEQ ID NO: 9), 0.2 µM inner IgG V primer (SEQ ID NO: 10), 1 µM outer IgG C primer (SEQ ID NO: 11), 4 ng/µL ET SSB, 2% RNase inhibitor, and 4% Reverse transcriptase and thermostable polymerase. An emulsion comprising the beads and RT-PCR mix was formed using an emulsion generating device (IKKA ULTRA-TURRAX Tube Drive systems with DT-20 tubes). A DT-20 tube was placed on the emulsion-generating device and 750 µL of an oil mix comprising 4.5% Span-80, 0.4% Tween 80, 0.05% Triton X-100 in mineral oil was added to the tube. 250 µL of cold beads and RT-PCR mix was then added dropwise to the top of the oil layer in the DT-20 tube. Emulsions of the solution in the DT-20 tube were then formed using the emulsion-generating device. After making emulsions, the emulsion mix was divided into 100 µL aliquots into PCR tubes.

RT-PCR was then performed on the emulsion mix using the following thermocycle conditions sequentially:

| | | |
|---|---|---|
| 55° C. | 30 min | |
| 94° C. | 3 min | |
| 94° C. | 30 s | 17 cycles; |
| 65° C. to 57° C. | 3 min | −0.5° C. anneal per cycle |
| 68° C. | 1 min | |
| 94° C. | 30 s | 26 cycles |
| 57° C. | 3 min | [43 cycles total] |
| 68° C. | 1 min | |
| 68° C. | 2 min | |
| 4° C. | ∞ | |

After PCR, 100 µL of ethyl acetate was added to each tube and the solution was mixed with a pipette. The broken emulsions were then transferred to a 1.5 mL tube and pulse vortexed to mix. The solution was then centrifuged at full speed for 1 minute and the upper layer (supernatant) was removed. The tube was then placed on a magnet and the lower layer (aqueous phase) comprising the amplification product was transferred to new 2 mL tube without beads. A QIAquick PCR Purification Kit from Qiagen was then used to extract amplified DNA from the aqueous phase. The isolated amplified DNA includes a library of scFv inserts (scFv encoding polynucleotide) (i.e., SEQ ID NO: 13, from the control Adalumimab sequence) that will be used in the generation of expression constructs.

Generation of Expression Constructs pPIC9 vector (Life Technologies) was modified to include a portion of the human IgG1 sequence (SEQ ID NO: 12). The concentration of scFv inserts generated above was determined. 0.02 pmol of pPIC9_IgG1 vector was combined with 0.04 pmol of isolated scFv inserts (e.g., example SEQ ID NO: 13) in water to a final volume of 5 µL. 5 µL of 2× Gibson Assembly Master Mix (New England Biolabs) was added to the vector/scFv insert solution. The samples were then incubated at 50° C. for 60 minutes to generate a circularized construct of the scFv insert in the pPIC9_IgG1 vector.

A wild type AOX1 promoter was then added to the circularized construct to induce expression of the scFv insert as follows: 0.02 pmol of the circularized construct comprising the scFv insert and the pPIC9_IgG1 vector was combined in water to a final volume of 5 µL. 5 µL of 2× Gibson Assembly Master Mix (New England Biolabs) was added to the vector/scFv insert solution. The samples were then incubated at 50° C. for 60 minutes to generate a circularized construct of the scFv insert in the pPIC9_IgG1 vector.

The circularized construct was then linearized with XhoI restriction endonuclease from NEB to generate linearized scFv plasmid DNA.

Protein Expression in Yeast

Frozen competent yeast cells were thawed on ice. 40 µL of yeast cells were transferred to a tube containing 10 µL of 0.1 µg/µL linearized scFv plasmid DNA. The DNA and yeast cell mixture was incubated on ice for 5 minutes. The mixture was then electroporated at 1.5 kV, 200 Omega, and 25 uF. 1 mL of recovery medium (50% 1M sorbitol, 50% yeast extract peptone dextrose (YPD)) was then added to the mixture, and the tube was shaken at 200 rpm for 1 hour at 30° C. The yeast was then plated onto RDB minus His agar selection plates and incubated overnight at 30° C. A transformed yeast colony was then selected form the plate and added to 50 mL BMGY medium. The yeast was shaken at 200 rpm overnight (at least 20 hours) at 30° C., until reaching an OD600 of between 5 and 10. Then, the culture was centrifuged at 2000×g for 5 minutes, and the supernatant was removed. Yeast cells were then resuspended in 50 mL BMMY medium and grown for 24 hours at 30° C. while being shaken at 200 rpm. After 24 hours, methanol was added to the yeast culture to a final concentration of 1% volume by volume. The yeast culture was then centrifuged at 2000×g for 5 minutes to collect the scFv library in the supernatant. The supernatant was collected, filtered, and stored at 4° C. for further purification and analysis.

Figure 5:
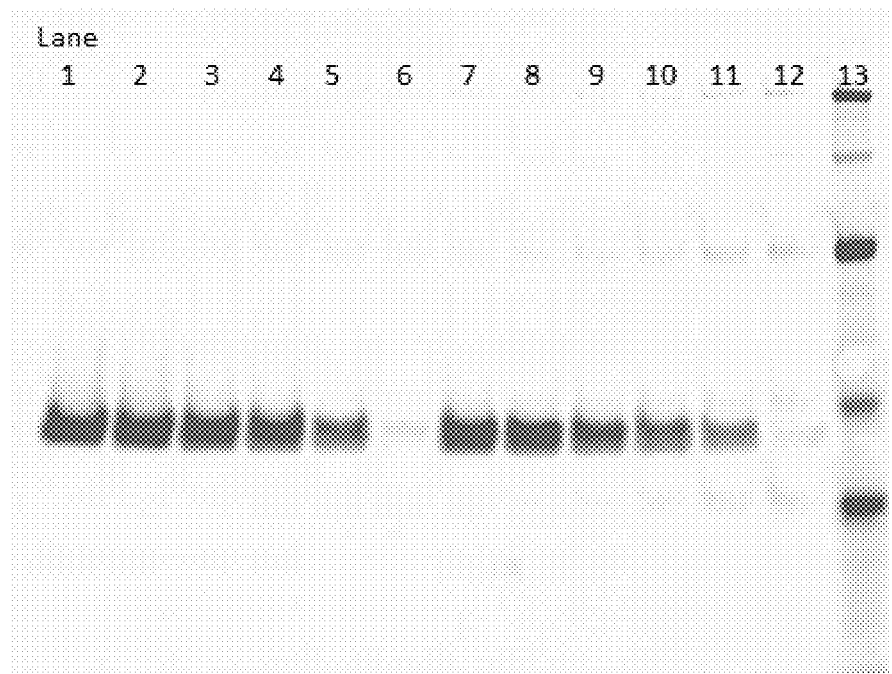
FIG. 5 shows a Western blot showing expression of scFv antibody fragments in yeast over time. scFvs are tagged with the peptide marker c-myc. scFvs are tagged with the peptide marker c-myc. Lanes 1-6 are induced using the wild type AOX1 promoter at 72 hr, 66 hr, 47 hr, 24 hr, and 18 hr respectively. Lanes 7-12 are the same time points as Lanes 1-6, respectively, but using a different promoter. Lane 13 is a size marker.

A portion of the supernatant collected from yeast was run on a Western blot as shown in FIG. 5 to show the scFv library. scFvs are tagged with the peptide marker c-myc. scFvs are tagged with the peptide marker c-myc. Lanes 1-6 are induced using the wild type AOX1 promoter at 72 hr, 66 hr, 47 hr, 24 hr, and 18 hr respectively. Lanes 7-12 are the same time points as Lanes 1-6, respectively, but using a different promoter. Lane 14 is a size marker.

Example 2

Antibody Generation

Generation of Expression Constructs

An scFv library (including, e.g., SEQ ID NO: 1) was linearized by PCR using standard PCR methods and forward and reverse primers (e.g., SEQ ID NO: 4,5). An insert containing a second AOX1 promoter was synthesized by a gene synthesis vendor (IDT). A insert was then added to the circularized construct to induce expression of the full length antibody, such that the vector would now contain two AOX1 promoters, i.e., one each for heavy and light chain immunoglobulin. The new library was engineered as follows: 0.02 pmol of the linearized construct comprising the pPIC9_IgG1_scFv vector was combined with 0.04 pmol of the promoter insert (SEQ ID NO: 3) in water to a final volume of 5 µL. 5 µL of 2× Gibson Assembly Master Mix (New England Biolabs) was added to the scFv vector/promoter solution. The samples were then incubated at 50° C. for 60 minutes to generate a circularized construct of the promoter insert in the pPIC9_IgG1_scFv vector.

Protein Expression in Yeast

Frozen competent yeast cells were thawed on ice. 40 µL of yeast cells were transferred to a tube containing 10 µL of 0.1 µg/µL linearized full length antibody DNA from above. The DNA and yeast cell mixture was incubated on ice for 5 minutes. The mixture was then electroporated at 1.5 kV, 200 Omega, and 25 uF. 1 mL of recovery medium (50% 1M sorbitol, 50% YPD) was then added to the mixture, and the tube was shaken at 200 rpm for 1 hour at 30° C. The yeast was then plated onto RDB minus His agar selection plates and incubated. A transformed yeast colony was then selected form the plate and added to 50 mL BMGY medium. The yeast was shaken at 200 rpm overnight (at least 20 hours) at 30° C., until reaching an OD600 of between 5 and 10. Then, the culture was centrifuged at 2000×g for 5 minutes, and the supernatant was removed. Yeast cells were then resuspended in 50 mL BMMY medium and grown for 24 hours at 30° C. while being shaken at 200 rpm. After 24 hours, methanol was added to the yeast culture to a final concentration of 1% weight by volume. The yeast culture was then centrifuged at 2000×g for 5 minutes to collect the recombinant antibody library in the supernatant. The supernatant was collected, filtered, and stored at 4° C. for further purification and analysis.

Figure 6:
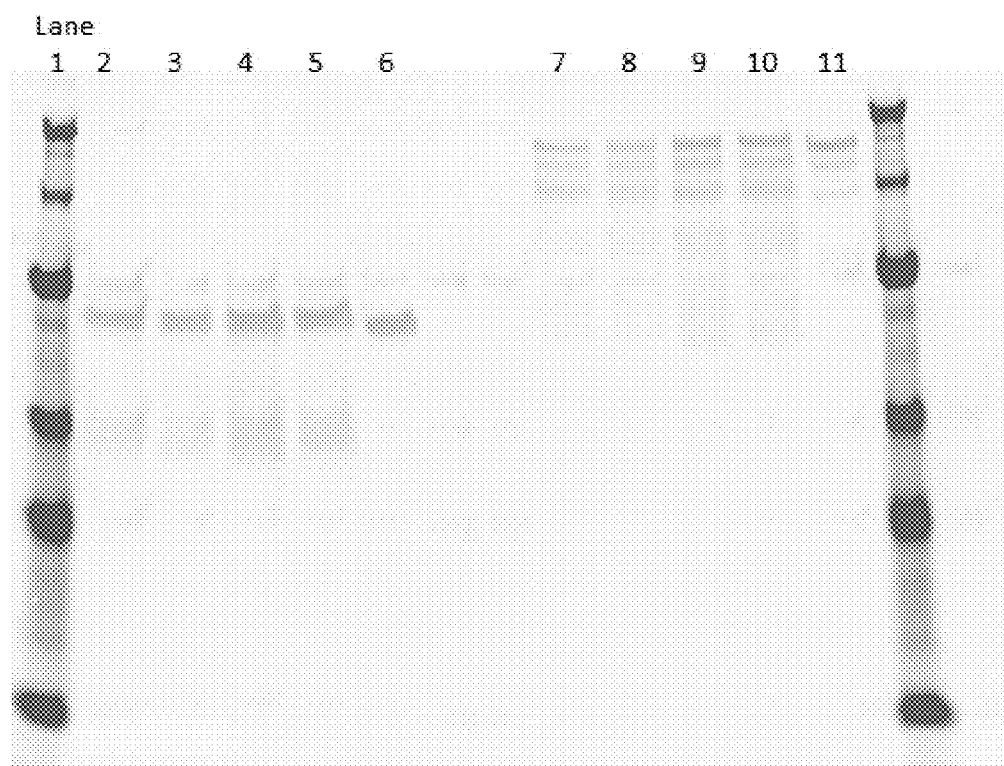
FIG. 6 shows a Western blot showing expression of full-length antibodies in yeast. Lane 1 is a size marker. Lane 1 is a size marker. Lanes 2-5 are antibodies expressed in yeast, Lane 6 is antibody expressed in CHO, all under reduced conditions. Lanes 7-10 are the same antibodies expressed in yeast, Lane 11 is antibody expressed in CHO, under non-reduced conditions.

A portion of the supernatant collected from yeast was run on a Western blot as show the recombinant antibody library. FIG. 6 shows the resulting Western blot, showing expression of full-length antibodies in yeast. Lane 1 is a size marker. Lanes 2-5 are antibodies expressed in yeast, Lane 6 is antibody expressed in CHO cells, all under reduced conditions. Lanes 7-10 are the same antibodies expressed in yeast, Lane 11 is antibody expressed in CHO cells, under non-reduced conditions.

Example 3

Monoclonal Antibody Drug Discovery

Mice are immunized with a protein or other kind of antigen of interest. Single B cells from the mice are isolated and linked complexes of paired heavy and light chain variable regions are produced in vitro. B cell isolation is performed using droplet microfluidics or isolation into physical containers such as 96-well plates. The fusion construct libraries are inserted into and expressed in host cells on the surface as scFv. The engineered cells are screened for binding to sequence variants of the antigen of interest. RNA or DNA is extracted from engineered cells with binding affinity for the antigen of interest, and the RNA or DNA is sequenced to determine the immunoglobulin content of the selected cells. The linked Ig complexes amplified from the antigen-selected engineered cells are cloned en masse into plasmid vectors to produce a library of plasmid vectors comprising the recombinant fusion construct.

To study the function of these Ig complexes as full-length antibodies, the linker sequence between the heavy and light chain variable region polynucleotide sequences is replaced with a polynucleotide sequence that encodes immunoglobulin protein subunits required for expression of a full length antibody comprising the paired heavy and light chain variable regions produced in vitro. The inserted polynucleotide sequence also includes a transcriptional promoter that drives expression of one of the Ig chains. The library of protein expression constructs is introduced into a population of host cells to produce a library of engineered cells that express a library of recombinant full-length antibodies. The library of recombinant full-length antibodies is analyzed to discover monoclonal antibodies that are of use therapeutically. To perform this analysis, the subpopulations of engineered cells is isolated and isolated pools are screened for affinity against a particular antigen. Pools of engineered cells that show activity against an antigen are divided into single cells, and screened again for affinity against a single antigen. Cell isolation is performed using droplet microfluidics or isolation into physical containers such as 96-well plates. Recombinant antibodies with affinity for antigens of interest are discovered.

Example 4

Polyclonal Antibody Therapeutics

In this example, IVIg is produced in recombinant cells rather than extracted from donor plasma. Primary B cells is collected from thousands of human donors. Single cells from each donor are isolated and linked complexes of paired heavy and light chain variable regions from each cell are produced in vitro. B cell isolation is performed using droplet microfluidics or isolation into physical containers such as 96-well plates. The resulting fused protein complexes is cloned en masse into plasmid vectors to produce a library of fused protein encoding plasmid vectors. The linker sequence between the heavy and light chain variable region polynucleotide sequences is replaced with a linker construct that includes a transcriptional promoter and any required portions of heavy or light chain Ig, i.e., part of a constant region that was not included in the original scFv expression construct. The library of fused protein expression constructs is introduced into a population of cells to produce a library of engineered cells that express a library of recombinant antibody proteins. The recombinant antibody proteins comprises variable light and heavy immunoglobulin domains from the source primary B cells. The pool of antibody proteins can be used as a recombinant replacement for IVIg.

The diversity of the B cells, the initial library of paired heavy and light chain Ig, the library of protein expression constructs, and/or the engineered host cells will be determined using massively parallel DNA sequencing.

Example 5

Polyclonal Antibody Pneumococcus Therapeutics

B cell donors are injected with a vaccine against pneumococcus. B cells are isolated from these donors. Then, large libraries of polynucleotide protein expression constructs are made from each of the individual B cells. B cell isolation is performed using droplet microfluidics, or isolation into physical containers such as 96-well plates. The protein expression constructs are introduced into engineered cells en masse and then protein libraries are produced from the engineered cells. These protein libraries contain hundreds, thousands, or millions of individual antibodies, depending on the diversity of the starting input B cells. The resulting protein libraries are used as targeted polyclonal therapeutics against particular pathogens, such as CMV.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method for preparing a recombinant immunoglobulin library, comprising:
providing primary immune cells from at least one mammalian donor;
isolating in a plurality of monodisperse droplets single immune cells from said primary immune cells;
generating a plurality of recombinant fusion polynucleotides each comprising a first polynucleotide encoding a heavy chain variable domain and a second polynucleotide encoding a light chain variable domain, wherein said heavy chain variable domain and light chain variable domain on each of said plurality of recombinant fusion polynucleotides are a cognate pair from one of said isolated primary immune cells, wherein each of said plurality of recombinant fusion polynucleotides further comprise a linker polynucleotide linking said first and second polynucleotides;
circularizing each of said plurality of linear recombinant fusion polynucleotides; and
inserting a third polynucleotide comprising a sequence encoding a promoter and a sequence encoding a constant region between said first and second polynucleotide in each of said circularized recombinant fusion polynucleotides, thereby generating at least 1,000 unique recombinant immunoglobulin expression constructs, thereby generating a recombinant immunoglobulin library.

2. The method of claim 1, further comprising:
inserting said at least 1,000 recombinant immunoglobulin expression constructs into a plurality of host cells; and
expressing said at least 1,000 recombinant immunoglobulin expression constructs in said plurality of host cells, thereby generating a recombinant immunoglobulin library comprising at least 1,000 unique recombinant immunoglobulins, wherein each of said at least 1,000 unique recombinant immunoglobulins comprises a linked heavy chain and light chain variable domain cognate pair from a single isolated cell, thereby generating a recombinant immunoglobulin library.

3. The method of claim 2, wherein said recombinant immunoglobulin library encodes at least 10,000, 100,000, or 1,000,000 unique recombinant immunoglobulin proteins.

4. The method of claim 1, wherein said at least one mammalian donor is selected based on a medical criterion.

5. The method of claim 4, wherein said medical criterion comprises a heightened immune response to hepatitis B, rabies, tetanus toxin, varicella-zoster, cytomegalovirus, or pneumococcus.

6. The method of claim 1, wherein said at least one mammalian donor was exposed to an antigen of interest or a pathogen.

7. The method of claim 6, wherein said antigen of interest is a tumor antigen selected from the group consisting of: CD19, CD20, CD22, CD52, epidermal growth factor receptor (EGFR), human epidermal growth factor receptor 2 (HER2), tumor necrosis factor receptor superfamily, member 10a (TRAILR1), receptor activator of nuclear factor kappa-B ligand (RANKL), insulin-like growth factor 1 receptor (IGF1R), epithelial cell adhesion molecule (EpCAM), carcinoembryonic antigen (CEA), and mucin 5AC.

8. The method of claim 6, wherein said antigen of interest is an autoimmune antigen selected from the group consisting of: thrombin, nicotinic acetylcholine receptor, thyroglobulin, TSH receptor, glutamate decarboxylase, phospholipase-A2-receptor (PLA2R), and muscle specific kinase (MUSK).

9. The method of claim 1, wherein said at least one mammalian donor was immunized against a pathogen.

10. The method of claim 1, wherein said at least one mammalian donor has an autoimmune disease or cancer.

11. The method of claim 1, wherein said at least one mammalian donor has idiopathic (immune) thrombocytopenic purpura (ITP), Kawasaki's vasculitis, B cell chronic lymphocytic leukemia (CLL), or primary immunodeficiencies.

12. The method of claim 1, wherein said recombinant immunoglobulin expression construct is an expression vector.

13. The method of claim 5, wherein said medical criterion comprises a heightened immune response to pneumococcus or hepatitis B.

14. The method of claim 7, wherein said antigen of interest is a tumor antigen selected from the group consisting of: epithelial cell adhesion molecule (EpCAM) and epidermal growth factor receptor (EGFR).

15. The method of claim 8, wherein said antigen of interest is an autoimmune antigen selected from the group consisting of: TSH receptor and thyroglobulin.

16. The method of claim 11, wherein said at least one mammalian donor has primary immunodeficiencies or B cell chronic lymphocytic leukemia (CLL).

* * * * *

SEQUENCE LISTING

```
<160> NUMBER OF SEQ ID NOS: 13

<210> SEQ ID NO 1
<211> LENGTH: 4634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cttcagtaat gtcttgtttc ttttgttgca gtggtgagcc attttgactt cgtgaaagtt      60
tctttagaat agttgtttcc agaggccaaa cattccaccc gtagtaaagt gcaagcgtag     120
gaagaccaag actggcataa atcaggtata agtgtcgagc actggcaggt gatcttctga     180
aagtttctac tagcagataa gatccagtag tcatgcatat ggcaacaatg taccgtgtgg     240
atctaagaac gcgtcctact aaccttcgca ttcgttggtc cagtttgttg ttatcgatca     300
acgtgacaag gttgtcgatt ccgcgtaagc atgcataccc aaggacgcct gttgcaattc     360
caagtgagcc agttccaaca atctttgtaa tattagagca cttcattgtg ttgcgcttga     420
aagtaaaatg cgaacaaatt aagagataat ctcgaaaccg cgacttcaaa cgccaatatg     480
atgtgcggca cacaataagc gttcatatcc gctgggtgac tttctcgctt taaaaaatta     540
tccgaaaaaa tttttctagag tgttgttact ttatacttcc ggctcgtata atacgacaag     600
gtgtaaggag gactaaacca tggctaaact cacctctgct gttccagtcc tgactgctcg     660
tgatgttgct ggtgctgttg agttctggac tgatagactc ggtttctccc gtgacttcgt     720
agaggacgac tttgccggtg ttgtacgtga cgacgttacc ctgttcatct ccgcagttca     780
ggaccaggtt gtgccagaca acactctggc atgggtatgg gttcgtggtc tggacgaact     840
gtacgctgag tggtctgagg tcgtgtctac caacttccgt gatgcatctg gtccagctat     900
gaccgagatc ggtgaacagc cctggggtcg tgagtttgca ctgcgtgatc cagctggtaa     960
ctgcgtgcat ttcgtcgcag aagaacagga ctaacaattg acaccttacg attatttaga    1020
gagtatttat tagttttatt gtatgtatac ggatgtttta ttatctattt atgcccttat    1080
attctgtaac tatccaaaag tcctatctta tcaagccagc aatctatgtc cgcgaacgtc    1140
aactaaaaat aagcttttta tgctgttctc tcttttttc ccttcggtat aattatacct    1200
tgcatccaca gattctcctg ccaaattttg cataatcctt tacaacatgg ctatatggga    1260
gcacttagcg ccctccaaaa cccatattgc ctacgcatgt ataggtgttt tttccacaat    1320
attttctctg tgctctcttt ttattaaaga gaagctctat atcggagaag cttctgtggc    1380
```

```
cgttatattc ggccttatcg tgggaccaca ttgcctgaat tggtttgccc cggaagattg   1440
gggaaacttg gatctgatta ccttagctgc aggtaccact gagcgtcaga ccccgtagaa   1500
aagatcaaag gatcttcttg agatcctttt tttctgcgcg taatctgctg cttgcaaaca   1560
aaaaaaccac cgctaccagc ggtggttttgt ttgccggatc aagagctacc aactcttttt   1620
ccgaaggtaa ctggcttcag cagagcgcag ataccaaata ctgttcttct agtgtagccg   1680
tagttaggcc accacttcaa gaactctgta gcaccgccta catacctcgc tctgctaatc   1740
ctgttaccag tggctgctgc cagtggcgat aagtcgtgtc ttaccggggtt ggactcaaga   1800 cgatagttac cggataaggc gcagcggtcg ggctgaacgg ggggttcgtg cacacagccc   1860
agcttggagc gaacgaccta caccgaactg agatacctac agcgtgagct atgagaaagc   1920
gccacgcttc ccgaagggag aaaggcggac aggtatccgg taagcggcag gtcggaaca   1980 ggagagcgca cgagggagct tccaggggga aacgcctggt atctttatag tcctgtcggg   2040
tttcgccacc tctgacttga gcgtcgattt ttgtgatgct cgtcaggggg gcggagccta   2100
tggaaaaacg ccagcaacgc ggccttttta cggttcctgg cctttttgctg ccttttgct   2160 cacatgttct ttcctgcggt acccagatcc aattcccgct ttgactgcct gaaatctcca   2220
tcgcctacaa tgatgacatt tggatttggt tgactcatgt tggtattgtg aaatagacgc   2280
agatcgggaa cactgaaaaa tacacagtta ttattcattt aaataacatc caaagacgaa   2340
aggttgaatg aaacctttt gccatccgac atccacaggt ccattctcac ataagtgc   2400 caaacgcaac aggaggggat acactagcag cagaccgttg caaacgcagg acctccactc   2460
ctcttctcct caacacccac ttttgccatc gaaaaaccag cccagttatt gggcttgatt   2520
ggagctcgct cattccaatt ccttctatta ggctactaac accatgactt tattagcctg   2580
tctatcctgg cccccctggc gaggttcatg tttgtttatt tccgaatgca caagctccg   2640 cattaccccc gaacatcact ccagatgagg gctttctgag tgtggggtca aatagtttca   2700
tgttccccaa atgcccaaa actgacagtt taaacgctgt cttggaacct aatatgacaa   2760
aagcgtgatc tcatccaaga tgaactaagt ttggttcgtt gaaatgctaa cggccagttg   2820
gtcaaaaaga aacttccaaa agtcggcata ccgtttgtct tgtttggtat tgattgacga   2880
atgctcaaaa ataatctcat taatgcttag cgcagtctct ctatcgcttc tgaaccccgg   2940
tgcacctgtg ccgaaacgca aatgggggaaa caccgctttt ttggatgatt atgcattgtc   3000
tccacattgt atgcttccaa gattctggtg ggaatactgc tgatagccta acgttcatga   3060
tcaaaattta actgttctaa cccctacttg acagcaatat ataaacagaa ggaagctgcc   3120
ctgtcttaaa cctttttttt tatcatcatt attagcttac tttcataatt gcgactggtt   3180
ccaattgaca agcttttgat tttaacgact tttaacgaca acttgagaag atcaaaaaac   3240
aactaattat tgaaagaatt ccgaaacgat gagattccca tctattttca ccgctgtctt   3300
gttcgctgcc tcctctgcat tggctgcccc tgttaacact accactgaag acgagactgc   3360
tcaaattcca gctgaagcag ttatcggtta ctctgacctt gagggtgatt tcgacgtcgc   3420
tgttttgcct ttctctaact ccactaacaa cggtttgttg ttcattaaca ccactatcgc   3480
ttccattgct gctaaggaag agggtgtctc tctcgagaaa agagaggccg aagctgacat   3540
ccagatgacc cagtctccat cctccctgtc tgcatctgta ggggacagag tcaccatcac   3600
ttgtcgggca agtcagggca tcagaaatta cttagcctgg tatcagcaaa aaccagggaa   3660
agcccctaag ctcctgatct atgctgcatc cactttgcaa tcaggggtcc catctcggtt   3720
cagtggcagt ggatctggga cagatttcac tctcaccatc agcagcctac agcctgaaga   3780
```

```
tgttgcaact tattactgtc aaaggtataa ccgtgcaccg tatactttg gccaggggac    3840 caaggtggaa atcaaacgaa ctgtggctgc accatctgtc ggcggatcct ctaggtcaag    3900
ttccagcggc ggcggtggca gcggaggcgg cggtgaggtg cagctggtgg agtctggggg    3960
aggcttggta cagcccggca ggtccctgag actctcctgt gcggcctctg gattcacctt    4020
tgatgattat gccatgcact gggtccggca agctccaggg aagggcctgg aatgggtctc    4080
agctatcact tggaatagtg gtcacataga ctatgcggac tctgtggagg gccgattcac    4140
catctccaga gacaacgcca agaactccct gtatctgcaa atgaacagtc tgagagctga    4200
ggatacggcc gtatattact gtgcgaaagt ctcgtacctt agcaccgcgt cctcccttga    4260 ctattgggc caaggtaccc tggtcaccgt ctcgagtgcc tccaccaagg gcccatcgt    4320 cttcgaacag aagctcatct cagaagagga tctgtaaagg ggcggccgct caagaggatg    4380
tcagaatgcc atttgcctga gagatgcagg cttcattttt gatactttt tatttgtaac    4440 ctatatagta taggatttt tttgtcattt tgtttcttct cgtacgagct tgctcctgat    4500
cagcctatct cgcagcagat gaatatcttg tggtaggggt ttgggaaaat cattcgagtt    4560
tgatgttttt cttggtattt cccactcctc ttcagagtac agaagattaa gtgaaccttt    4620
cgtttgtgcg gatc                                                     4634

<210> SEQ ID NO 2
<211> LENGTH: 7457
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cttcagtaat gtcttgtttc ttttgttgca gtggtgagcc attttgactt cgtgaaagtt      60
tctttagaat agttgtttcc agaggccaaa cattccaccc gtagtaaagt gcaagcgtag     120
gaagaccaag actggcataa atcaggtata agtgtcgagc actggcaggt gatcttctga     180
aagtttctac tagcagataa gatccagtag tcatgcatat ggcaacaatg taccgtgtgg     240
atctaagaac gcgtcctact aaccttcgca ttcgttggtc cagtttgttg ttatcgatca     300
acgtgacaag gttgtcgatt ccgcgtaagc atgcataccc aaggacgcct gttgcaattc     360
caagtgagcc agttccaaca atctttgtaa tattagagca cttcattgtg ttgcgcttga     420
aagtaaaatg cgaacaaatt aagagataat ctcgaaaccg cgacttcaaa cgccaatatg     480
atgtgcggca cacaataagc gttcatatcc gctgggtgac tttctcgctt taaaaaatta     540
tccgaaaaaa ttttctagag tgttgttact ttatacttcc ggctcgtata atacgacaag     600
gtgtaaggag gactaaacca tggctaaact cacctctgct gttccagtcc tgactgctcg     660
tgatgttgct ggtgctgttg agttctggac tgatagactc ggtttctccc gtgacttcgt     720
agaggacgac tttgccggtg ttgtacgtga cgacgttacc ctgttcatct ccgcagttca     780
ggaccaggtt gtgccagaca acactctggc atgggtatgg ttcgtggtc tggacgaact     840 gtacgctgag tggtctgagg tcgtgtctac caacttccgt gatgcatctg gtccagctat     900
gaccgagatc ggtgaacagc cctggggtcg tgagtttgca ctgcgtgatc agctggtaa      960 ctgcgtgcat tcgtcgcag aagaacagga ctaacaattg acaccttacg attatttaga     1020
gagtatttat tagttttatt gtatgtatac ggatgtttta ttatcttatt atgccctat     1080 attctgtaac tatccaaaag tcctatctta tcaagccagc aatctatgtc cgcgaacgtc     1140
```

```
aactaaaaat aagcttttta tgctgttctc tcttttttc ccttcggtat aattatacct   1200
tgcatccaca gattctcctg ccaaattttg cataatcctt tacaacatgg ctatatggga   1260
gcacttagcg ccctccaaaa cccatattgc ctacgcatgt ataggtgttt tttccacaat   1320
attttctctg tgctctcttt ttattaaaga gaagctctat atcggagaag cttctgtggc   1380
cgttatattc ggccttatcg tgggaccaca ttgcctgaat tggtttgccc cggaagattg   1440
gggaaacttg gatctgatta ccttagctgc aggtaccact gagcgtcaga ccccgtagaa   1500
aagatcaaag gatcttcttg agatccttt  tttctgcgcg taatctgctg cttgcaaaca   1560
aaaaaaccac cgctaccagc ggtggtttgt ttgccggatc aagagctacc aactcttttt   1620
ccgaaggtaa ctggcttcag cagagcgcag ataccaaata ctgttcttct agtgtagccg   1680
tagttaggcc accacttcaa gaactctgta gcaccgccta catacctcgc tctgctaatc   1740
ctgttaccag tggctgctgc cagtggcgat aagtcgtgtc ttaccgggtt ggactcaaga   1800
cgatagttac cggataaggc gcagcggtcg ggctgaacgg ggggttcgtg cacacagccc   1860
agcttggagc gaacgaccta caccgaactg agatacctac agcgtgagct atgagaaagc   1920
gccacgcttc ccgaagggag aaaggcggac aggtatccgg taagcggcag ggtcggaaca   1980
ggagagcgca cgagggagct tccaggggga aacgcctggt atctttatag tcctgtcggg   2040
tttcgccacc tctgacttga gcgtcgattt tgtgatgct  cgtcagggg  gcggagccta   2100
tggaaaaacg ccagcaacgc ggcctttta  cggttcctgg ccttttgctg gccttttgct   2160
cacatgttct ttcctgcggt acccagatcc aattcccgct ttgactgcct gaaatctcca   2220
tcgcctacaa tgatgacatt tggatttggt tgactcatgt tggtattgtg aaatagacgc   2280
agatcgggaa cactgaaaaa tacacagtta ttattcattt aaataacatc aaagacgaa    2340
aggttgaatg aaaccttttt gccatccgac atccacaggt ccattctcac ataagtgc     2400
caaacgcaac aggaggggat acactagcag cagaccgttg caaacgcagg acctccactc   2460
ctcttctcct caacacccac ttttgccatc gaaaaaccag cccagttatt gggcttgatt   2520
ggagctcgct cattccaatt ccttctatta ggctactaac accatgactt tattagcctg   2580
tctatcctgg ccccccctggc gaggttcatg tttgtttatt tccgaatgca acaagctccg   2640
cattacaccc gaacatcact ccagatgagg gcttctgag  tgtggggtca aatagtttca   2700
tgttccccaa atgcccaaa  actgacagtt taaacgctgt cttggaacct aatatgacaa   2760
aagcgtgatc tcatccaaga tgaactaagt ttggttcgtt gaaatgctaa cggccagttg   2820
gtcaaaaaga aacttccaaa agtcggcata ccgtttgtct tgtttggtat tgattgacga   2880
atgctcaaaa ataatctcat taatgcttag cgcagtctct ctatcgcttc tgaaccccgg   2940
tgcacctgtg ccgaaacgca aatggggaaa cacccgcttt ttggatgatt atgcattgtc   3000
tccacattgt atgcttccaa gattctggtg ggaatactgc tgatagccta acgttcatga   3060
tcaaaattta actgttctaa cccctacttg acagcaatat ataaacagaa ggaagctgcc   3120
ctgtcttaaa ccttttttt  tatcatcatt attagcttac tttcataatt gcgactggtt   3180
ccaattgaca agcttttgat tttaacgact tttaacgaca acttgagaag atcaaaaaac   3240
aactaattat tgaaagaatt ccgaaacgat gagattccca tctatttca  ccgctgtctt   3300
gttcgctgcc tcctctgcat tggctgcccc tgttaacact accactgaag acgagactgc   3360
tcaaattcca gctgaagcag ttatcggtta ctctgacctt gagggtgatt tcgacgtcgc   3420
tgttttgcct ttctctaact ccactaacaa cggtttgttg ttcattaaca ccactatcgc   3480
```

```
ttccattgct gctaaggaag agggtgtctc tctcgagaaa agagaggccg aagctgacat    3540
ccagatgacc cagtctccat cctccctgtc tgcatctgta ggggacagag tcaccatcac    3600
ttgtcgggca agtcagggca tcagaaatta cttagcctgg tatcagcaaa aaccagggaa    3660
agcccctaag ctcctgatct atgctgcatc cactttgcaa tcaggggtcc catctcggtt    3720
cagtggcagt ggatctggga cagatttcac tctcaccatc agcagcctac agcctgaaga    3780
tgttgcaact tattactgtc aaaggtataa ccgtgcaccg tacttttgg ccaggggac     3840
caaggtggaa atcaaacgaa ctgtggctgc accatctgtc ttcatcttcc cgccatctga    3900
tgagcagttg aaatctggaa ctgcctctgt tgtgtgcctg ctgaataact tctatcccag    3960
agaggccaaa gtacagtgga aggtggataa cgccctccaa tcgggtaact cccaggagag    4020
tgtcacagag caggacagca aggacagcac ctacagcctc agcagcaccc tgacgctgag    4080
caaagcagac tacgagaaac acaaagtcta cgcctgcgaa gtcacccatc agggcctgag    4140
ctcgcccgtc acaaagagct caacagggg agagtgttaa aggggcggcc gctcaagagg    4200
atgtcagaat gccatttgcc tgagagatgc aggcttcatt tttgatactt ttttatttgt    4260
aacctatata gtataggatt ttttttgtca ttttgtttct tctcgtacga gcttgctcct    4320
gatcagccta tctcgcagca gatgaatatc ttgtggtagg ggtttgggaa atcattcga    4380
gtttgatgtt tttcttggta tttcccactc ctcttcagag tacagaagat taagtgaaac    4440
cttcgtttgt gcgtgttctt tcctgcggta cccagatcca attcccgctt tgactgcctg    4500
aaatctccat cgcctacaat gatgacattt ggatttggtt gactcatgtt ggtattgtga    4560
aatagacgca gatcgggaac actgaaaaat acacagttat tattcattta aataacatcc    4620
aaagacgaaa ggttgaatga aacctttttg ccatccgaca tccacaggtc cattctcaca    4680
cataagtgcc aaacgcaaca ggaggggata cactagcagc agaccgttgc aaacgcagga    4740
cctccactcc tcttctcctc aacacccact tttgccatcg aaaaaccagc ccagttattg    4800
ggcttgattg gagctcgctc attccaattc cttctattag gctactaaca ccatgacttt    4860
attagcctgt ctatcctggc ccccctggcg aggttcatgt ttgtttattt ccgaatgcaa    4920
caagctccgc attacacccg aacatcactc cagatgaggg cttttctgag tgtggggtcaa   4980
atagtttcat gttccccaaa tggcccaaaa ctgacagttt aaacgctgtc ttggaaccta    5040
atatgacaaa agcgtgatct catccaagat gaactaagtt tggttcgttg aaatgctaac    5100
ggccagttgg tcaaaaagaa acttccaaaa gtcggcatac cgtttgtctt gtttggtatt    5160
gattgacgaa tgctcaaaaa taatctcatt aatgcttagc gcagtctctc tatcgcttct    5220
gaaccccggt gcacctgtgc cgaaacgcaa atggggaaac acccgctttt tggatgatta    5280
tgcattgtct ccacattgta tgcttccaag attctggtgg gaatactgct gatagcctaa    5340
cgttcatgat caaaatttaa ctgttctaac ccctacttga cagcaatata taaacagaag    5400
gaagctgccc tgtcttaaac ctttttttt atcatcatta ttagcttact ttcataattg    5460
cgactggttc caattgacaa gcttttgatt ttaacgactt ttaacgacaa cttgagaaga    5520
tcaaaaaaca actaattatt gaaagaattc cgaaacgatg agattcccat ctattttcac    5580
cgctgtcttg ttcgctgcct cctctgcatt ggctgcccct gttaacacta ccactgaaga    5640
cgagactgct caaattccag ctgaagcagt tatcggttac tctgaccttg agggtgattt    5700
cgacgtcgct gttttgcctt tctctaactc cactaacaac ggtttgttgt tcattaacac    5760
cactatcgct tccattgctg ctaaggaaga gggtgtctct ctcgagaaaa gagaggccga    5820
agctgaggtg cagctggtgg agtctggggg aggcttggta cagcccggca ggtccctgag    5880
```

```
actctcctgt gcggcctctg gattcacctt tgatgattat gccatgcact gggtccggca    5940
agctccaggg aagggcctgg aatgggtctc agctatcact tggaatagtg gtcacataga    6000
ctatgcggac tctgtggagg gccgattcac catctccaga gacaacgcca agaactccct    6060
gtatctgcaa atgaacagtc tgagagctga ggatacggcc gtatattact gtgcgaaagt    6120
ctcgtacctt agcaccgcgt cctcccttga ctattgggc caaggtaccc tggtcaccgt    6180
ctcgagtgcc tccaccaagg gcccatcggt cttccccctg gcacctcct ccaagagcac    6240 ctctggggc acagcggccc tgggctgcct ggtcaaggac tacttccccg aaccggtgac    6300
ggtgtcgtgg aactcaggcg ccctgaccag cggcgtgcac accttcccgg ctgtcctaca    6360
gtcctcagga ctctactccc tcagcagcgt ggtgaccgtg ccctccagca gcttgggcac    6420
ccagacctac atctgcaacg tgaatcacaa gcccagcaac accaaggtgg acaagaaagt    6480
tgagcccaaa tcttgtgaca aaactcacac atgcccaccg tgcccagcac ctgaactcct    6540
ggggggaccg tcagtcttcc tcttcccccc aaaacccaag gacaccctca tgatctcccg    6600
gacccctgag gtcacatgcg tggtggtgga cgtgagccac gaagaccctg aggtcaagtt    6660
caactggtac gtggacggcg tggaggtgca taatgccaag acaaagccgc gggaggagca    6720
gtacaacagc acgtaccgtg tggtcagcgt cctcaccgtc ctgcaccagg actggctgaa    6780
tggcaaggag tacaagtgca aggtctccaa caaagccctc ccagccccca tcgagaaaac    6840
catctccaaa gccaaagggc agccccgaga accacaggtg tacaccctgc ccccatcccg    6900
ggatgagctg accaagaacc aggtcagcct gacctgcctg gtcaaaggct tctatcccag    6960
cgacatcgcc gtggagtggg agagcaatgg gcagccggag aacaactaca agaccacgcc    7020
tcccgtgctg gactccgacg gctccttctt cctctacagc aagctcaccg tggacaagag    7080
caggtggcag caggggaacg tcttctcatg ctccgtgatg catgaggctc tgcacaacca    7140
ctacacgcag aagagcctct ccctgtctcc gggtaaataa aggggcggcc gctcaagagg    7200
atgtcagaat gccatttgcc tgagagatgc aggcttcatt tttgatactt ttttatttgt    7260
aacctatata gtataggatt ttttttgtca ttttgtttct tctcgtacga gcttgctcct    7320
gatcagccta tctcgcagca gatgaatatc ttgtggtagg ggtttgggaa aatcattcga    7380
gtttgatgtt tttcttggta tttcccactc ctcttcagag tacagaagat taagtgaaac    7440
cttcgtttgt gcggatc                                                   7457
```

<210> SEQ ID NO 3
<211> LENGTH: 1944
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
ttcatcttcc cgccatctga tgagcagttg aaatctggaa ctgcctctgt tgtgtgcctg      60
ctgaataact tctatcccag agaggccaaa gtacagtgga aggtggataa cgccctccaa     120
tcgggtaact cccaggagag tgtcacagag caggacagca aggacagcac ctacagcctc     180
agcagcaccc tgacgctgag caaagcagac tacgagaaac acaaagtcta cgcctgcgaa     240
gtcacccatc agggcctgag ctcgcccgtc acaaagagct tcaacagggg agagtgttaa     300
aggggcggcc gctcaagagg atgtcagaat gccatttgcc tgagagatgc aggcttcatt     360
tttgatactt ttttatttgt aacctatata gtataggatt ttttttgtca ttttgtttct     420
```

-continued

```
tctcgtacga gcttgctcct gatcagccta tctcgcagca gatgaatatc ttgtggtagg        480
ggtttgggaa aatcattcga gtttgatgtt tttcttggta tttcccactc ctcttcagag        540
tacagaagat taagtgaaac cttcgtttgt gcgtgttctt tcctgcggta cccagatcca        600
attcccgctt tgactgcctg aaatctccat cgcctacaat gatgacattt ggatttggtt        660
gactcatgtt ggtattgtga aatagacgca gatcgggaac actgaaaaat acacagttat        720
tattcattta aataacatcc aaagacgaaa ggttgaatga aacctttttg ccatccgaca        780
tccacaggtc cattctcaca cataagtgcc aaacgcaaca ggaggggata cactagcagc        840
agaccgttgc aaacgcagga cctccactcc tcttctcctc aacacccact tttgccatcg        900
aaaaaccagc ccagttattg ggcttgattg gagctcgctc attccaattc cttctattag        960
gctactaaca ccatgacttt attagcctgt ctatcctggc cccctggcg aggttcatgt       1020
ttgtttattt ccgaatgcaa caagctccgc attacacccg aacatcactc cagatgaggg       1080
ctttctgagt gtggggtcaa atagtttcat gttccccaaa tggcccaaaa ctgacagttt       1140
aaacgctgtc ttggaaccta atatgacaaa agcgtgatct catccaagat gaactaagtt       1200
tggttcgttg aaatgctaac ggccagttgg tcaaaaagaa acttccaaaa gtcggcatac       1260
cgtttgtctt gtttggtatt gattgacgaa tgctcaaaaa taatctcatt aatgcttagc       1320
gcagtctctc tatcgcttct gaaccccggt gcacctgtgc cgaaacgcaa atggggaaac       1380
acccgctttt tggatgatta tgcattgtct ccacattgta tgcttccaag attctggtgg       1440
gaatactgct gatagcctaa cgttcatgat caaaatttaa ctgttctaac ccctacttga       1500
cagcaatata taaacagaag gaagctgccc tgtcttaaac cttttttttt atcatcatta       1560
ttagcttact ttcataattg cgactggttc caattgacaa gcttttgatt ttaacgactt       1620
ttaacgacaa cttgagaaga tcaaaaaaca actaattatt gaaagaattc cgaaacgatg       1680
agattcccat ctattttcac cgctgtcttg ttcgctgcct cctctgcatt ggctgccoct       1740
gttaacacta ccactgaaga cgagactgct caaattccag ctgaagcagt tatcggttac       1800
tctgaccttg agggtgattt cgacgtcgct gttttgcctt tctctaactc cactaacaac       1860
ggtttgttgt tcattaacac cactatcgct tccattgctg ctaaggaaga gggtgtctct       1920
ctcgagaaaa gagaggccga agct                                              1944
```

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gtctctctcg agaaaagaga ggccgaagct saggtgcagc tggtggag        48

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
caactgctca tcagatggcg ggaagatgaa gacagatggt gcagccacag t        51

```
<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctgccacctg ctcttgtcca cggtgagctt gctgt                                35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tgatgggtga cttcgcaggc gtagagtttg tgttt                                35

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggactggaca tccagwtgac ccagtct                                         27

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccgccgctg gaacttgacc tagaggatcc gccgacagat ggtgcagcca cagt           54

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggtcaagtt ccagcggcgg cggtggcagc ggaggcggcg gtsaggtgca gctggtggag     60

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccryggcttt gtcttggcat                                                 20
```

<210> SEQ ID NO 12
<211> LENGTH: 8956
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggccccctg gcgaggttca tgtttgttta      300
tttccgaatg caacaagctc cgcattacac ccgaacatca ctccagatga gggctttctg     360
agtgtggggt caaatagttt catgttcccc aaatggccca aaactgacag tttaaacgct     420
gtcttggaac ctaatatgac aaaagcgtga tctcatccaa gatgaactaa gtttggttcg     480
ttgaaatgct aacggccagt tggtcaaaaa gaaacttcca aaagtcgcca taccgtttgt     540
cttgtttggt attgattgac gaatgctcaa aaataatctc attaatgctt agcgcagtct     600
ctctatcgct tctgaacccc ggtgcacctg tgccgaaacg caaatgggga acacccgct      660
ttttggatga ttatgcattg tctccacatt gtatgcttcc aagattctgg tgggaatact     720
gctgatagcc taacgttcat gatcaaaatt taactgttct aacccctact tgacagcaat     780
atataaacag aaggaagctg ccctgtctta aacctttttt tttatcatca ttattagctt     840
actttcataa ttgcgactgg ttccaattga caagcttttg attttaacga cttttaacga     900
caacttgaga agatcaaaaa acaactaatt attcgaagga tccaaacgat gagatttcct     960
tcaattttta ctgcagtttt attcgcagca tcctccgcat tagctgctcc agtcaacact    1020
acaacagaag atgaaacggc acaaattccg gctgaagctg tcatcggtta ctcagattta    1080
gaagggggatt tcgatgttgc tgttttgcca ttttccaaca gcacaaataa cgggttattg    1140
tttataaata ctactattgc cagcattgct gctaaagaag aagggggtatc tctcgagaaa    1200
agagaggctg aagctcccct ggcacccctc ctccaagagca cctctggggg cacagcggcc    1260
ctgggctgcc tggtcaagga ctacttcccc gaaccggtga cggtgtcgtg gaactcaggc    1320
gccctgacca gcggcgtgca caccttcccg gctgtcctac agtcctcagg actctactcc    1380
ctcagcagcg tggtgaccgt gccctccagc agcttgggca cccagaccta catctgcaac    1440
gtgaatcaca agcccagcaa caccaaggtg gacaagaaag ttgagcccaa atcttgtgac    1500
aaaactcaca catgcccacc gtgcccagca cctgaactcc tggggggacc gtcagtcttc    1560
ctcttccccc caaaacccaa ggacaccctc atgatctccc ggaccctga ggtcacatgc      1620
gtggtggtgg acgtgagcca cgaagaccct gaggtcaagt tcaactggta cgtggacggc    1680
gtggaggtgc ataatgccaa gacaaagccg cgggaggagc agtacaacag cacgtaccgt    1740
gtggtcagcg tcctcaccgt cctgcaccag gactggctga atggcaagga gtacaagtgc    1800
aaggtctcca acaaagccct cccagccccc atcgagaaaa ccatctccaa agccaaaggg    1860
cagccccgag aaccacaggt gtacaccctg cccccatccc gggatgagct gaccaagaac    1920
caggtcagcc tgacctgcct ggtcaaaggc ttctatccca gcgacatcgc cgtggagtgg    1980
gagagcaatg ggcagccgga gaacaactac aagaccacgc ctcccgtgct ggactccgac    2040
ggctccttct tcctctacag caagctcacc gtggacaaga gcaggtggca gcaggggaac    2100
```

```
gtcttctcat gctccgtgat gcatgaggct ctgcacaacc actacacgca gaagagcctc    2160
tccctgtctc cgggtaaata attcgcctta gacatgactg ttcctcagtt caagttgggc    2220
acttacgaga agaccggtct tgctagattc taatcaagag gatgtcagaa tgccatttgc    2280
ctgagagatg caggcttcat ttttgatact ttttttatttg taacctatat agtataggat    2340 ttttttttgtc atttttgtttc ttctcgtacg agcttgctcc tgatcagcct atctcgcagc    2400
tgatgaatat cttgtggtag gggtttggga aaatcattcg agtttgatgt ttttcttggt    2460
atttcccact cctcttcaga gtacagaaga ttaagtgaga agttcgtttg tgcaagctta    2520
tcgataagct ttaatgcggt agtttatcac agttaaattg ctaacgcagt caggcaccgt    2580
gtatgaaatc taacaatgcg ctcatcgtca tcctcggcac cgtcaccctg gatgctgtag    2640
gcataggctt ggttatgccg gtactgccgg gcctcttgcg ggatatcgtc cattccgaca    2700
gcatcgccag tcactatggc gtgctgctag cgctatatgc gttgatgcaa tttctatgcg    2760
cacccgttct cggagcactg tccgaccgct ttggccgccg cccagtcctg ctcgcttcgc    2820
tacttggagc cactatcgac tacgcgatca tggcgaccac acccgtcctg tggatctatc    2880
gaatctaaat gtaagttaaa atctctaaat aattaaataa gtcccagttt ctccatacga    2940
accttaacag cattgcggtg agcatctaga ccttcaacag cagccagatc catcactgct    3000
tggccaatat gtttcagtcc ctcaggagtt acgtcttgtg aagtgatgaa cttctggaag    3060
gttgcagtgt taactccgct gtattgacgg gcatatccgt acgttggcaa agtgtggttg    3120
gtaccggagg agtaatctcc acaactctct ggagagtagg caccaacaaa cacagatcca    3180
gcgtgttgta cttgatcaac ataagaagaa gcattctcga tttgcaggat caagtgttca    3240
ggagcgtact gattggacat ttccaaagcc tgctcgtagg ttgcaaccga tagggttgta    3300
gagtgtgcaa tacacttgcg tacaatttca acccttggca actgcacagc ttggttgtga    3360
acagcatctt caattctggc aagctccttg tctgtcatat cgacagccaa cagaatcacc    3420
tgggaatcaa taccatgttc agcttgagac agaaggtctg aggcaacgaa atctggatca    3480
gcgtatttat cagcaataac tagaacttca gaaggcccag caggcatgtc aatactacac    3540
agggctgatg tgtcattttg aaccatcatc ttggcagcag taacgaactg gtttcctgga    3600
ccaaatattt tgtcacactt aggaacagtt tctgttccgt aagccatagc agctactgcc    3660
tgggcgcctc ctgctagcac gatacactta gcaccaacct tgtgggcaac gtagatgact    3720
tctggggtaa gggtaccatc cttcttaggt ggagatgcaa aaacaatttc tttgcaacca    3780
gcaactttgg caggaacacc cagcatcagg gaagtggaag gcagaattgc ggttccacca    3840
ggaatataga ggccaacttt ctcaataggt cttgcaaaac gagagcagac tacaccaggg    3900
caagtctcaa cttgcaacgt ctccgttagt tgagcttcat ggaatttcct gacgttatct    3960
atagagagat caatggctct cttaacgtta tctggcaatt gcataagttc ctctgggaaa    4020
ggagcttcta acacaggtgt cttcaaagcg actccatcaa acttggcagt tagttctaaa    4080
agggctttgt caccattttg acgaacattg tcgacaattg gtttgactaa ttccataatc    4140
tgttccgttt tctggatagg acgacgaagg gcatcttcaa tttcttgtga ggaggcctta    4200
gaaacgtcaa ttttgcacaa ttcaaatacga ccttcagaag ggacttcttt aggtttggat    4260
tcttctttag gttgttcctt ggtgtatcct ggcttggcat ctcctttcct tctagtgacc    4320
tttagggact tcatatccag gtttctctcc acctcgtcca acgtcacacc gtacttggca    4380
catctaacta atgcaaaata aaataagtca gcacattccc aggctatatc ttccttggat    4440
```

```
ttagcttctg caagttcatc agcttcctcc ctaattttag cgttcaacaa aacttcgtcg    4500
tcaaataacc gtttggtata agaaccttct ggagcattgc tcttacgatc ccacaaggtg    4560
gcttccatgg ctctaagacc cttttgattgg ccaaaacagg aagtgcgttc caagtgacag    4620
aaaccaacac ctgtttgttc aaccacaaat ttcaagcagt ctccatcaca atccaattcg    4680 atcccagca acttttgagt tgctccagat gtagcacctt tataccacaa accgtgacga    4740
cgagattggt agactccagt ttgtgtcctt atagcctccg gaatagactt tttggacgag    4800
tacaccaggc ccaacgagta attagaagag tcagccacca aagtagtgaa tagaccatcg    4860
gggcggtcag tagtcaaaga cgccaacaaa atttcactga cagggaactt tttgacatct    4920
tcagaaagtt cgtattcagt agtcaattgc cgagcatcaa taatggggat tataccagaa    4980
gcaacagtgg aagtcacatc taccaacttt gcggtctcag aaaaagcata aacagttcta    5040
ctaccgccat tagtgaaact tttcaaatcg cccagtggag aagaaaaagg cacagcgata    5100
ctagcattag cgggcaagga tgcaaccttta tcaaccaggg tcctatagat aaccctagcg    5160
cctgggatca tcctttggac aactctttct gccaaatcta ggtccaaaat cacttcattg    5220
ataccattat tgtacaactt gagcaagttg tcgatcagct cctcaaattg gtcctctgta    5280
acggatgact caacttgcac attaacttga agctcagtcg attgagtgaa cttgatcagg    5340
ttgtgcagct ggtcagcagc atagggaaac acggcttttc ctaccaaact caaggaatta    5400
tcaaactctg caacacttgc gtatgcaggt agcaagggaa atgtcatact tgaagtcgga    5460
cagtgagtgt agtcttgaga aattctgaag ccgtattttt attatcagtg agtcagtcat    5520
caggagatcc tctacgccgg acgcatcgtg gccggcatca ccggcgccac aggtgcggtt    5580
gctggcgcct atatcgccga catcaccgat ggggaagatc gggctcgcca cttcgggctc    5640
atgagcgctt gtttcggcgt gggtatggtg gcaggccccg tggccggggg actgttgggc    5700
gccatctcct tgcatgcacc attccttgcg gcggcggtgc tcaacggcct caacctacta    5760
ctgggctgct tcctaatgca ggagtcgcat aaggagagc gtcgagtatc tatgattgga    5820
agtatgggaa tggtgatacc cgcattcttc agtgtcttga ggtctcctat cagattatgc    5880
ccaactaaag caaccggagg aggagatttc atggtaaatt tctctgactt ttggtcatca    5940
gtagactcga actgtgagac tatctcggtt atgacagcag aaatgtcctt cttggagaca    6000
gtaaatgaag tcccaccaat aaagaaatcc ttgttatcag gaacaaactt cttgtttcga    6060
actttttcgg tgccttgaac tataaaatgt agagtggata tgtcgggtag gaatggagcg    6120
ggcaaatgct taccttctgg accttcaaga ggtatgtagg gtttgtagat actgatgcca    6180
acttcagtga caacgttgct atttcgttca aaccattccg aatccagaga atcaaagtt    6240 gtttgtctac tattgatcca agccagtgcg gtcttgaaac tgacaatagt gtgctcgtgt    6300
tttgaggtca tctttgtatg aataaatcta gtctttgatc taaataatct tgacgagcca    6360
aggcgataaa tacccaaatc taaaactctt ttaaaacgtt aaaaggacaa gtatgtctgc    6420
ctgtattaaa ccccaaatca gctcgtagtc tgatcctcat caacttgagg ggcactatct    6480
tgttttagag aaatttgcgg agatgcgata tcgagaaaaa ggtacgctga ttttaaacgt    6540
gaaatttatc tcaagatctc tgcctcgcgc gtttcggtga tgacggtgaa aacctctgac    6600
acatgcagct cccggagacg gtcacagctt gtctgtaagc ggatgccggg agcagacaag    6660
cccgtcaggg cgcgtcagcg ggtgttggcg ggtgtcgggg cgcagccatg acccagtcac    6720
gtagcgatag cggagtgtat actggcttaa ctatgcggca tcagagcaga ttgtactgag    6780
agtgcaccat atgcggtgtg aaataccgca cagatgcgta aggagaaaat accgcatcag    6840
```

```
gcgctcttcc gcttcctcgc tcactgactc gctgcgctcg gtcgttcggc tgcggcgagc    6900
ggtatcagct cactcaaagg cggtaatacg gttatccaca gaatcagggg ataacgcagg    6960
aaagaacatg tgagcaaaag gccagcaaaa ggccaggaac cgtaaaaagg ccgcgttgct    7020
ggcgttttc cataggctcc gcccccctga cgagcatcac aaaaatcgac gctcaagtca    7080
gaggtggcga aacccgacag gactataaag ataccaggcg tttccccctg gaagctccct    7140
cgtgcgctct cctgttccga ccctgccgct taccggatac ctgtccgcct ttctcccttc    7200
gggaagcgtg gcgctttctc aatgctcacg ctgtaggtat ctcagttcgg tgtaggtcgt    7260
tcgctccaag ctgggctgtg tgcacgaacc ccccgttcag cccgaccgct gcgccttatc    7320
cggtaactat cgtcttgagt ccaacccggt aagacacgac ttatcgccac tggcagcagc    7380
cactggtaac aggattagca gagcgaggta tgtaggcggt gctacagagt tcttgaagtg    7440
gtggcctaac tacggctaca ctagaaggac agtatttggt atctgcgctc tgctgaagcc    7500
agttaccttc ggaaaaagag ttggtagctc ttgatccggc aaacaaacca ccgctggtag    7560
cggtggtttt tttgtttgca agcagcagat tacgcgcaga aaaaaggat ctcaagaaga    7620
tcctttgatc ttttctacgg ggtctgacgc tcagtggaac gaaaactcac gttaagggat    7680
tttggtcatg agattatcaa aaaggatctt cacctagatc cttttaaatt aaaaatgaag    7740
ttttaaatca atctaaagta tatatgagta aacttggtct gacagttacc aatgcttaat    7800
cagtgaggca cctatctcag cgatctgtct atttcgttca tccatagttg cctgactccc    7860
cgtcgtgtag ataactacga tacgggaggg cttaccatct ggccccagtg ctgcaatgat    7920
accgcgagac ccacgctcac cggctccaga tttatcagca ataaaccagc cagccggaag    7980
ggccgagcgc agaagtggtc ctgcaacttt atccgcctcc atccagtcta ttaattgttg    8040
ccgggaagct agagtaagta gttcgccagt taatagtttg cgcaacgttg ttgccattgc    8100
tgcaggcatc gtggtgtcac gctcgtcgtt tggtatggct tcattcagct ccggttccca    8160
acgatcaagg cgagttacat gatccccat gttgtgcaaa aaagcggtta gctccttcgg    8220
tcctccgatc gttgtcagaa gtaagttggc cgcagtgtta tcactcatgg ttatggcagc    8280
actgcataat tctcttactg tcatgccatc cgtaagatgc ttttctgtga ctggtgagta    8340
ctcaaccaag tcattctgag aatagtgtat gcggcgaccg agttgctctt gcccggcgtc    8400
aacacgggat aataccgcgc cacatagcag aactttaaaa gtgctcatca ttggaaaacg    8460
ttcttcgggg cgaaaactct caaggatctt accgctgttg agatccagtt cgatgtaacc    8520
cactcgtgca cccaactgat cttcagcatc ttttactttc accagcgttt ctgggtgagc    8580
aaaaacagga aggcaaaatg ccgcaaaaaa gggaataagg gcgacacgga aatgttgaat    8640
actcatactc ttcctttttc aatattattg aagcatttat cagggttatt gtctcatgag    8700
cggatacata tttgaatgta tttagaaaaa taaacaaata ggggttccgc gcacatttcc    8760
ccgaaaagtg ccacctgacg tctaagaaac cattattatc atgacattaa cctataaaaa    8820
taggcgtatc acgaggccct ttcgtcttca agaattaatt ctcatgtttg acagcttatc    8880
atcgataagc tgactcatgt tggtattgtg aaatagacgc agatcgggaa cactgaaaaa    8940
taacagttat tattcg                                                    8956
```

<210> SEQ ID NO 13
<211> LENGTH: 789
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 13

```
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa acgaactgtg gctgcaccat ctgtcggcgg atcctctagg     360
tcaagttcca gcggcggcgg tggcagcgga ggcggcggtg aggtgcagct ggtggagtct     420
gggggaggct tggtacagcc cggcaggtcc ctgagactct cctgtgcggc ctctggattc     480
acctttgatg attatgccat gcactgggtc cggcaagctc cagggaaggg cctggaatgg     540
gtctcagcta tcacttggaa tagtggtcac atagactatg cggactctgt ggagggccga     600
ttcaccatct ccagagacaa cgccaagaac tccctgtatc tgcaaatgaa cagtctgaga     660
gctgaggata cggccgtata ttactgtgcg aaagtctcgt accttagcac cgcgtcctcc     720
cttgactatt ggggccaagg tacctggtc accgtctcga gtgcctccac caagggccca     780
tcggtcttc                                                             789
```